US008088571B2

(12) United States Patent
Seidah et al.

(10) Patent No.: US 8,088,571 B2
(45) Date of Patent: Jan. 3, 2012

(54) METHODS OF REDUCING A VIRAL INFECTION AND KITS THEREFORE

(75) Inventors: Nabil G. Seidah, Verdun (CA); Patrick Labonté, Laval (CA)

(73) Assignees: Institut de Recherches Cliniques de Montreal, Montreal (CA); Institut National de la Recherche Scientifique, Quebec (CA)

( * ) Notice: Subject to any disclaimer, the term of this patent is extended or adjusted under 35 U.S.C. 154(b) by 89 days.

(21) Appl. No.: 12/234,027

(22) Filed: Sep. 19, 2008

(65) Prior Publication Data
US 2009/0104209 A1 Apr. 23, 2009

Related U.S. Application Data

(60) Provisional application No. 60/974,106, filed on Sep. 21, 2007.

(30) Foreign Application Priority Data

Sep. 21, 2007 (CA) ...................................... 2603615

(51) Int. Cl.
C12Q 1/70 (2006.01)
A61K 38/00 (2006.01)
A01N 37/18 (2006.01)
A61P 1/16 (2006.01)

(52) U.S. Cl. ............... 435/5; 514/1.1; 514/2.3; 514/3.7; 514/4.3

(58) Field of Classification Search ........................ None
See application file for complete search history.

(56) References Cited

U.S. PATENT DOCUMENTS

| 6,025,155 | A | 2/2000 | Hadlaczky et al. |
| 6,077,677 | A | 6/2000 | Hodgson et al. |
| 6,204,023 | B1 | 3/2001 | Robinson et al. |
| 2002/0160970 | A1 | 10/2002 | Hadlaczky et al. |
| 2003/0083293 | A1 | 5/2003 | Hadlaczky et al. |

FOREIGN PATENT DOCUMENTS
WO  WO 2007/128121  11/2007

OTHER PUBLICATIONS

Details for Cell MOLT-4 (ATCC), Lonza AG, printed on Jun. 11, 2010.*
Jeong et al., "Sterol-dependent regulation of proprotein convertase subtilisin/kexin type 9 expression by sterol-regulatory element binding protein-2," Journal of Lipid Research, vol. 49, pp. 399-409 (Feb. 2008).*
Labonté et al., "PCSK9 impedes hepatitis C virus infection in vitro and modulates liver CD81 expression," Hepatology, vol. 50 No. 1, pp. 17-25 (Jul. 2009).*
Machida et al., "Hepatitis C Virus E2-CD81 Interaction Induces Hypermutation of the Immunoglobulin Gene in B Cells," Journal of Virology, vol. 79 No. 13, pp. 8079-8089 (Jul. 2005).*
Mousavi et al., "The unique role of proprotein convertase subtilisin/kexin 9 in cholesterol homeostasis," Journal of Internal Medicine, vol. 266 No. 6, pp. 507-519 (Sep. 2009).*
Qian et al., "Secreted PCSK9 downregulates low density lipoprotein receptor through receptor-mediated endocytosis," Journal of Lipid Research, vol. 48 No. 7, pp. 1488-1498 (Epub Apr. 20, 2007).*
Abifadel et al, "Mutations in PCSK9 cause autosomal dominant hypercholesterolemia", Nature Genetics (2003), vol. 34, No. 2, p. 154-156.
Agnello et al, "Hepatitis C virus and other Flaviviridae viruses enter cells via low density lipoprotein receptor", PNAS (1999), vol. 96, No. 22, p. 12766-12771.
Akazawa et al, "CD81 Expression Is Important for the Permissiveness of Huh7 Cell Clones for Heterogeneous . . . ", Journal of Virology (2007), vol. 81, No. 10, p. 5036-5045.
Allard et al, "Novel Mutations of the PCSK9 Gene Cause Variable Phenotype of Autosomal Dominant Hypercholesterolemia", Human Mutation (2005), Mutation in Brief #854 Online.
Anderson et al, "Inhibition of HIV-1 gp160-dependent Membrane Fusion by a Furin-directed X1-Antitrypsin Variant", Journal of Biol. Chem. (1993), vol. 268, No. 33: 24887-24891.
André et al, "Characterization of Low- and Very-Low-Density Hepatitis C Virus RNA-Containing Particles", Journal of Virology (2002), vol. 76, No. 14, p. 6919-6928.
Andréo et al, "Lipoprotein lipase mediates hepatitis C Virus (HCV) cell entry and inhibits HCV infection", Cellular Microbiology (2007), vol. 9 (10), p. 2445-2456.
Attie, A. D., "The Mystery of PCSK9", Arteriosclerosis, Thrombosis, and Vascular Biology (2004), vol. 24, p. 1337-1339.
Attie et al, "Dual regulation of the LDL receptor—Some clarity and new questions", Cell Metabolism (2005), vol. 1, p. 290-292.
Bartenschlager et al, "Novel insights into hepatitis C virus replication and persistence", Advances in Virus Research, Germany (2004), vol., 63, p. 71-180.
Barth et al, "Viral and Cellular Determinants of the Hepatitis C Virus Envelope-Heparan Sulfate Interaction", Journal of Virology (2006), vol. 80, p. 10579-10590.
Bartosch et al, "Cell entry of hepatitis C Virus", Elsevier/Virology (2006), vol. 348, p. 1-12.
Benjannet et al, "NARC-1/PCSK9 and Its Natural Mutants", The Journal of Biological Chemistry (2004), vol. 279, No. 47, p. 48865-48875.
Benjannet et al, "The Proprotein Convertase (PC) PCSK9 Is Inactivated by Furin and/or PC5/6A", The Journal of Biological Chemistry (2006), vol. 281, No. 41, p. 30561-30572.

(Continued)

*Primary Examiner* — Jeffrey S. Parkin
*Assistant Examiner* — Louise Humphrey
(74) *Attorney, Agent, or Firm* — Goudreau Gage Dubuc; Julie Gauvreau

(57) ABSTRACT

A method for treating and/or preventing a proprotein convertase subtilisin/kexin type 9 preproprotein (PCSK9)-susceptible viral infection comprising increasing a PCSK9 activity and/or expression in a biological system infected by the virus, whereby the increased PCSK9 activity and/or expression treats and/or prevents the viral infection in the biological system. Methods of classifying subjects, methods of screening and kits therefore.

5 Claims, 13 Drawing Sheets

OTHER PUBLICATIONS

Benjannet et al, "a-Antitrypsin Portland Inhibits Processing of Precursors Mediated by . . . ", The Journal of Biological of Chemistry (1997), vol. 272, No. 42, p. 26210-26218.

Berditchevski et al, "Tetraspanins as Regulators of Protein Trafficking", Traffic (2007), vol. 8, p. 89-96.

Berge et al, "Missense Mutations in the PCSK9 Gene Are Associated With Hypocholesterolemia . . . ", Arteriosclerosis, Thrombosis and Vascular Biology (2006), vol. 26, p. 1094-1100.

Beyer et al, "Endoproteolytic Processing of the Lymphocytic Choriomeningitis Virus Glycoprotein by the Subtilase SKI-1/S1P", Journal of Virology (2003), p. 2866-2872.

Black et al, "An Overview of the Clinical Safety Profile of Atorvastatin (Lipitor), a New HMG-CoA Reductase Inhibitor", Arch Intern Med. (1998), vol. 158, p. 577-584.

Chandran et al, "Endosomal Proteolysis of the Ebola Virus Glycoprotein Is Necessary for Infection", Science AAAS (2005), vol. 308, p. 1643-1645.

Cheng et al, "Secreted Site-1 Protease Cleaves Peptides Corresponding to Luminal Loop of Sterol . . . ", The Journal of Biological Chemistry (1999), vol. 274, p. 22805-22812.

Cohen et al, "Low LDL cholesterol in individuals of African descent resulting from frequent nonsense mutations in PCSK9", Nature Genetics (2005), vol. 37, p. 161-165.

Diedrich, G., "How does hepatitis C virus enter cells?", FEBS Journal (2006), vol. 273, p. 3871-3885.

Dubuc et al, "Statins Upregulate PCSK9, the Gene Encoding the Proprotein Convertase . . . ", Arteriosclerosis, Thrombosis, and Vascular Biology (2004), vol. 24, p. 1454-1459.

Evans et al, "Claudin-1 is a hepatitis C virus co-receptor required for a late step in entry", Nature (2007), vol. 446, p. 801-805.

Fatemi, S. H., "Reelin Glycoprotein in Autism and Schizophrenia", International Review of Neurobiology (2005), vol. 71, p. 179-187.

Glenn et al, "Use of a Prenylation Inhibitor as a Novel Antiviral Agent", Journal of Virology (1998), vol. 72, No. 11, p. 9303-9306.

Gower et al, "Antiviral Activity of Lovastatin against Respiratory Syncytial Virus in Vivo . . . ", Antimicrobial Agents and Chemotherapy (2001), vol. 45, No. 4, p. 1231-1237.

Heller et al, "An in vitro model of hepatitis C virion production", PNAS (2005), vol. 102, No. 7, p. 2579-2583.

Henrich et al, "The crystal structure of the proprotein processing proteinase furin explains its stringent . . . ", Nature Structural Biology (2003), vol. 10, No. 7, p. 520-526.

Horton et al, "Combined analysis of oligonucleotide microarray data from transgenic and knockout mice identifies direct . . . ", PNAS (2003), vol. 100, No. 100, p. 12027-12032.

Jamshad et al, "Structural characterization of recombinant human CD81 produced in *Pichia pastoris*", Protein Expression & Purification (2008), vol. 57, p. 206-216.

Jin et al, "Proprotein Covertases Are Responsible for Proteolysis and Inactivation of . . . ", The Journal of Biological Chemistry (2005), vol. 280, No. 44, p. 36551-36559.

Jolly et al, "Human Immunodeficiency Virus Type 1 Assembly, Budding, and Cell-Cell Spread in T Cells Take Place . . . ", Journal of Virology (2007), vol. 81, No. 15, p. 7873-7884.

Kapadia et al, "Initiation of Hepatitis C Virus Infection Is Dependent on Cholesterol and Cooperativity between . . . ", Journal of Virology (2007), vol. 81, No. 1, p. 374-383.

Kohler et al, "Continuous cultures of fused cells secreting antibody of predefined specificity", Nature (1975), vol. 256, p. 495-497.

Kotowski et al, "A Spectrum of PCSK9 Alleles Contributes to Plasma Levels of Low-Density Lipoprotein . . . ", The American Journal of Human Genetics (2006), vol. 78, p. 410-422.

Krug, R. M., "Clues to the Virulence of H5N1 Viruses in Humans", Science, (2006), vol. 311, p. 1562-1563.

Lagace et al, "Secreted PCSK9 decreases the number of LKL receptors in hepatocytes and in . . .", The Journal of Clinical Investigation (2006), vol. 116, No. 11, p. 2995-3005.

Laird et al, "BACE1, a Major Determinant of Selective Vulnerability of the Brain to Amyloid-β Amyloidogenesis . . .", Journal of Neuroscience (2005), vol. 25, p. 11693-11709.

Lalanne et al, "Wild-type PCSK9 inhibits LDL clearance but does not affect apoB-containing lipoprotein production in . . . ", Journal of Lipid Research (2005), vol. 46, 1312-1319.

Lavillette et al, "Hepatitis C Virus Glycoproteins Mediate Low ph-dependent Membrane Fusion . . . ", The Journal of Biological Chemistry (2006), vol. 281, No. 7, p. 3909-3917.

Lazo, P. A., "Functional implications of tetraspanin proteins in cancer biology", Cancer Sci (2007), vol. 98, No. 11, p. 1666-1677.

Lenz et al, "The Lassa virus glycoprcitein precursor GP-C is proteolytically processed by subtilase SKI-1 / S1P", PNAS (2001), vol. 98, No. 22, p. 12701-12705.

Leren, T. P., "Mutations in the PCSK9 gene in Norwegian subjects with autosomal dominant hypercholesterolemia", Clinical Genetics (2004), vol. 65, p. 419-422.

Maxwell et al, "Adenoviral-mediated expression of Pcsk9 in mice results in a low-density lipoprotein receptor knockout phenotype", PNAS (2004), vol. 101, No. 18, p. 7100-7105.

Maxwell et al, "Overexpression of PCSK9 accelerates the degradation of the LDLR in a post-endoplasmic reticulum compartment", PNAS (2005), vol. 102, No. 6, p. 2069-2074.

Maxwell et al, "Novel putative SREBP and LXR target genes identified by microarray analysis in liver of . . . ", Journal of Lipid Research (2003), vol. 44, p. 2109-2119.

Naoumova et al, "Severe Hypercholesterolemia in Four British Families With the D374Y . . . ", Arteriosclerosis, Thrombosis, and Vascular Biology (2005), vol. 25, p. 2654-2660.

Nassoury et al, "The Cellular Trafficking of the Secretory Proprotein Convertase PCSK9 and Its Dependence on the LDLR", Traffic (2007), vol. 8, p. 718-732.

Nielsen et al, "Association between Hepatitis C Virus and Very-Low-Density Lipoprotein (VLDL)/LDL Analyzed in . . . ", Journal of Virology (2006), vol. 80, No. 5, p. 2418-2428.

Nour et al, "Structure-Function Analysis of the Prosegment of the Proprotein Convertase PC5A", The Journal of Biological Chemistry (2003), vol. 278, No. 5, p. 2886-2895.

Pager et al, "Cathepsin L Is Involved in Proteolytic Processing of the Hendra Virus Fusion Protein", Journal of Virology (2005), vol. 79, No. 20, p. 12714-12720.

Park et al, "Post-transcriptional Regulation of Low Density Lipoprotein Receptor Protein by . . . ", The Journal of Biological Chemistry (2004), vol. 279, No. 48, p. 50630-50638.

Petit et al, "Cell surface expression of LDL receptor in chronic hepatitis C: correlation with viral load", Am J Physiol Endocrinol Metab (2007), vol. 293, p. E416-E420.

Pileri et al, "Binding of Hepatitis C Virus to CD81", Science, (1998), vol. 282, p. 938-941.

Poirier et al, "The Proprotein Convertase PCSK9 Induces the Degradation of Low Density . . . ", The Journal of Biological Chemistry (2008), vol. 283, No. 4, p. 2363-2372.

Poynard et al, "Viral hepatitis C", The Lancet (2003), vol. 362, p. 2095-2100.

Pullikotil et al, "Development of Protein-based Inhibitors of the Proprotein of Convertase . . . ", The Journal of Biological Chemistry (2004), vol. 279, No. 17, p. 17338-17347.

Rashid et al, "Decreased plasma cholesterol and hypersensitivity to statins in mice lacking Pcsk9", PNAS (2005), vol. 102, No. 15, p. 5374-5379.

Rocha-Perugini et al, "The CD81 Partner EWI-2wint Inhibits Hepatitis C Virus Entry", PLoS ONE (2008), vol. 3, No. 4, e1866, p. 1-12.

Scarselli et al, "The human scavenger receptor class B type I is a novel candidate receptor for the hepatitis C virus", The EMBO Journal (2002), vol. 21, No. 19, p. 5017-5025.

Seidah, N. G., "Unexpected similarity between the cytosolic West Nile virus NS3 and the secretory furin-like serine . . . ", Biochemical Journal (2006), vol. 393, p. e1-e3.

Seidah et al, "Proprotein and prohormone convertases: a family of subtilases generating diverse bioactive . . . ", Brain Research Interactive, (1999), vol. 848, 45-62.

Seidah et al, "Precursor convertases in the secretory pathway, cytosol and extracellular milieu", Essays in Biochemistry (2002), vol. 38, p. 79-94.

Seidah et al, "The secretory proprotein convertase neural apoptosis-regulated convertase 1 (NARC-1): Liver regeneration . . . ", PNAS (2003), vol. 100, No. 3, p. 928-933.

Seidah et al, "The proprotein convertases and their implication in sterol and/or lipid metabolism", Biological Chemistry (2006), vol. 387, p. 871-877.

Seidah et al, "Mammalian subtilisin/kexin isozyme SKI-1: A widely expressed proprotein convertase with a unique cleavage specificity . . . ", PNAS (1999), vol. 96, p. 1321-1326.

Siagris et al, "Serum lipid pattern in chronic hepatitis C: histological and virological correlations", Journal of Viral Hepatitis (2006), vol. 13, p. 56-61.

Simmonds et al, "Consensus Proposals for a Unified System of Nomenclature of Hepatitis C Virus Genotypes", Hepatology (2005), vol. 42, No. 4, p. 962-973.

Simmons et al, "Inhibitors of cathepsin L prevent severe acute respiratory syndrome coronavirus entry", PNAS (2005), vol. 102, No. 33, p. 11876-11881.

Thomson et al, "Hepatitis C Virus infection", Clinical Microbiology and Infection (2005), vol. 11, No. 2, p. 86-94.

Timms et al, "A mutation in PCSK9 causing autosomal-dominiant hypercholesterolemia in a Utah pedigree", Hum Genet (2004), vol. 114, p. 349-353.

Vincent et al, "Crimean-Congo Hemorrhagic Fever Virus Glycoprotein Proteolytic Processing by Subtilase SKI-1", Journal of Virology (2003), vol. 77, No. 16, p. 8640-8649.

Wakita et al, "Production of infectious hepatitis C virus in tissue culture from a cloned viral genome", Nature Medecine (2005), vol. 11, No. 7, p. 791-796.

Wünschmann et al, "Characterization of Hepatitis C Virus (HCV) and HCV E2 Interactions with CD81 and the . . . ", Journal of Virology (2000), vol. 74, No. 21, p. 10055-10062.

Ye et al, "Disruption of hepatitis C virus RNA replication through inhibition of host protein geranylgeranylation", PNAS (2003), vol. 100, No. 26, p. 15865-15870.

Zaid et al, "Proprotein Convertase Subtilisin/Kexin Type 9 (PCSK9): Hepatocyte-Specific Low-Density Lipoprotein Receptor . . . ", Hepatology (2008), vol. 48, No. 2, p. 646-654.

Zeisel et al, "Scavenger Receptor Class B Type I Is a Key Host Factor for Hepatitis C Virus Infection Required for an . . . ", Hepatology (2007), vol. 46, No. 6, p. 1722-1731.

Zhong et al, "The Prosegments of Furin and PC7 as Potent Inhibitors of Proprotein Convertases", The Journal of Biological Cheministry (1999), vol. 274, No. 48, p. 33913-33920.

Benjannet et al., "Zymogen cleavage and effects on the low density lipoprotein (LDL) receptor and LDL cholesterol", The Journ. of Bio. Chem. (2004), 279(47): 48865-48875.

* cited by examiner

A

B

C

D

E

A. Human PCSK9 (with signal peptide) 1-692 and V5-tag

ATGGGCACCGTCAGCTCCAGGCGGTCCTGGTGGCCGCTGCCACTGCTGCTGCTGCTGCTGCTCCTGGGTCCCGCGGGCG
CCCGTGCGCAGGAGGACGAGGACGGCGACTACGAGGAGCTGGTGCTAGCCTTGCGTTCCGAGGAGGACGGCCTGGCCGAAGC
ACCCGAGCACGGAACCACAGCCACCTTCCACCGCTGCGCCAAGGATCCGTGGAGGTTGCCTGGCACCTACGTGGTGGTGCTG
AAGGAGGAGACCCACCTCTCGCAGTCAGAGCGCACTGCCCGCCGCCTGCAGGCCCAGGCTGCCCGCCGGGGATACCTCACCA
AGATCCTGCATGTCTTCCATGGCCTTCTTCCTGGCTTCCTGGTGAAGATGAGTGGCGACCTGCTGGAGCTGGCCTTGAAGTT
GCCCCATGTCGACTACATCGAGGAGGACTCCTCTGTCTTTGCCCAGAGCATCCCGTGGAACCTGGAGCGGATTACCCCTCCA
CGGTACCGGGCGGATGAATACCAGCCCCCCGACGGAGGCAGCCTGGTGGAGGTGTATCTCCTAGACACCAGCATACAGAGTG
ACCACCGGGAAATCGAGGGCAGGGTCATGGTCACCGACTTCGAGAATGTGCCCGAGGAGGACGGGACCCGCTTCCACAGACA
GGCCAGCAAGTGTGACAGTCATGGCACCCACCTGGCAGGGGTGGTCAGCGGCCGGGATGCCGGCGTGGCCAAGGGTGCCAGC
ATGCGCAGCCTGCGCGTGCTCAACTGCCAAGGGAAGGGCACGGTTAGCGGCACCCTCATAGGCCTGGAGTTTATTCGGAAAA
GCCAGCTGGTCCAGCCTGTGGGGCCACTGGTGGTGCTGCTGCCCCTGGCGGGTGGGTACAGCCGCGTCCTCAACGCCGCCTG
CCAGCGCCTGGCGAGGGCTGGGGTCGTGCTGGTCACCGCTGCCGGCAACTTCCGAGACGATGCCTGCCTCTACTCCCCAGCC
TCAGCTCCCGAGGTCATCACAGTTGGGGCCACCAATGCCCAGGACCAGCCGGTGACCCTGGGGACTTTGGGGACCAACTTTG
GCCGCTGTGTGGACCTCTTTGCCCCAGGGGAGGACATCATTGGTGCCTCCAGCGACTGCAGCACCTGCTTTGTGTCACAGAG
TGGGACATCACAGGCTGCTGCCCACGTGGCTGGCATTGCAGCCATGATGCTGTCTGCCGAGCCGGAGCTCACCCTGGCCGAG
TTGAGGCAGAGACTGATCCACTTCTCTGCCAAAGATGTCATCAATGAGGCCTGGTTCCCTGAGGACCAGCGGGTACTGACCC
CCAACCTGGTGGCCGCCCTGCCCCCCAGCACCCATGGGGCAGGTTGGCAGCTGTTTTGCAGGACTGTGTGGTCAGCACACTC
GGGGCCTACACGGATGGCCACAGCCATCGCCCGCTGCGCCCCAGATGAGGAGCTGCTGAGCTGCTCCAGTTTCTCCAGGAGT
GGGAAGCGGCGGGGCGAGCGCATGGAGGCCCAAGGGGGCAAGCTGGTCTGCCGGGCCCACAACGCTTTTGGGGGTGAGGGTG
TCTACGCCATTGCCAGGTGCTGCCTGCTACCCCAGGCCAACTGCAGCGTCCACACAGCTCCACCAGCTGAGGCCAGCATGGG
GACCCGTGTCCACTGCCACCAACAGGGCCACGTCCTCACAGGCTGCAGCTCCCACTGGGAGGTGGAGGACCTTGGCACCCAC
AAGCCGCCTGTGCTGAGGCCACGAGGTCAGCCCAACCAGTGCGTGGGCCACAGGGAGGCCAGCATCCACGCTTCCTGCTGCC
ATGCCCCAGGTCTGGAATGCAAAGTCAAGGAGCATGGAATCCCGGCCCCTCAGGAGCAGGTGACCGTGGCCTGCGAGGAGGG
CTGGACCCTGACTGGCTGCAGTGCCCTCCCTGGGACCTCCCACGTCCTGGGGGCCTACGCCGTAGACAACACGTGTGTAGTC
AGGAGCCGGGACGTCAGCACTACAGGCAGCACCAGCGAAGAGGCCGTGACAGCCGTTGCCATCTGCTGCCGGAGCCGGCACC
TGGCGCAGGCCTCCCAGGAGCTACAGACC*GGTAAGCCTATCCCTAACCCTCTCCTCGGTCTCGATTCTACGTGA*

MGTVSSRRSWWPLPLLLLLLLLGPAGARAQEDEDGDYEELVLALRSEEDGLAEAPEHGTTATFHRCAKDPWRLPGTYVVVL
KEETHLSQSERTARRLQAQAARRGYLTKILHVFHGLLPGFLVKMSGDLLELALKLPHVDYIEEDSSVFAQSIPWNLERITPP
RYRADEYQPPDGGSLVEVYLLDTSIQSDHREIEGRVMVTDFENVPEEDGTRFHRQASKCDSHGTHLAGVVSGRDAGVAKGAS
MRSLRVLNCQGKGTVSGTLIGLEFIRKSQLVQPVGPLVVLLPLAGGYSRVLNAACQRLARAGVVLVTAAGNFRDDACLYSPA
SAPEVITVGATNAQDQPVTLGTLGTNFGRCVDLFAPGEDIIGASSDCSTCFVSQSGTSQAAAHVAGIAAMMLSAEPELTLAE
LRQRLIHFSAKDVINEAWFPEDQRVLTPNLVAALPPSTHGAGWQLFCRTVWSAHSGPTRMATAIARCAPDEELLSCSSFSRS
GKRRGERMEAQGGKLVCRAHNAFGGEGVYAIARCCLLPQANCSVHTAPPAEASMGTRVHCHQQGHVLTGCSSHWEVEDLGTH
KPPVLRPRGQPNQCVGHREASIHASCCHAPGLECKVKEHGIPAPQEQVTVACEEGWTLTGCSALPGTSHVLGAYAVDNTCVV
RSRDVSTTGSTSEEAVTAVAICCRSRHLAQASQELQ*TGKPIPNPLLGLDST*

Figure 11

B. Human PCSK9-ACE2 with V5-tag

ATGGGCACCGTCAGCTCCAGGCGGTCCTGGTGGCCGCTGCCACTGCTGCTGCTGCTGCTGCTCCTGGGTCCCGCGGGCG
CCCGTGCGCAGGAGGACGAGGACGGCGACTACGAGGAGCTGGTGCTAGCCTTGCGTTCCGAGGAGGACGGCCTGGCCGAAGC
ACCCGAGCACGGAACCACAGCCACCTTCCACCGCTGCGCCAAGGATCCGTGGAGGTTGCCTGGCACCTACGTGGTGGTGCTG
AAGGAGGAGACCCACCTCTCGCAGTCAGAGCGCACTGCCCGCCGCCTGCAGGCCCAGGCTGCCCGCCGGGGATACCTCACCA
AGATCCTGCATGTCTTCCATGGCCTTCTTCCTGGCTTCCTGGTGAAGATGAGTGGCGACCTGCTGGAGCTGGCCTTGAAGTT
GCCCCATGTCGACTACATCGAGGAGGACTCCTCTGTCTTTGCCCAGAGCATCCCGTGGAACCTGGAGCGGATTACCCCTCCA
CGGTACCGGGCGGATGAATACCAGCCCCCCGACGGAGGCAGCCTGGTGGAGGTGTATCTCCTAGACACCAGCATACAGAGTG
ACCACCGGGAAATCGAGGGCAGGGTCATGGTCACCGACTTCGAGAATGTGCCCGAGGAGGACGGGACCCGCTTCCACAGACA
GGCCAGCAAGTGTGACAGTCATGGCACCCACCTGGCAGGGGTGGTCAGCGGCCGGGATGCCGGCGTGGCCAAGGGTGCCAGC
ATGCGCAGCCTGCGCGTGCTCAACTGCCAAGGGAAGGGCACGGTTAGCGGCACCCTCATAGGCCTGGAGTTTATTCGGAAAA
GCCAGCTGGTCCAGCCTGTGGGGCCACTGGTGGTGCTGCTGCCCCTGGCGGGTGGGTACAGCCGCGTCCTCAACGCCGCCTG
CCAGCGCCTGGCGAGGGCTGGGGTCGTGCTGGTCACCGCTGCCGGCAACTTCCGAGACGATGCCTGCCTCTACTCCCCAGCC
TCAGCTCCCGAGGTCATCACAGTTGGGGCCACCAATGCCCAGGACCAGCCGGTGACCCTGGGGACTTTGGGGACCAACTTTG
GCCGCTGTGTGGACCTCTTTGCCCCAGGGGAGGACATCATTGGTGCCTCCAGCGACTGCAGCACCTGCTTTGTGTCACAGAG
TGGGACATCACAGGCTGCTGCCCACGTGGCTGGCATTGCAGCCATGATGCTGTCTGCCGAGCCGGAGCTCACCCTGGCCGAG
TTGAGGCAGAGACTGATCCACTTCTCTGCCAAAGATGTCATCAATGAGGCCTGGTTCCCTGAGGACCAGCGGGTACTGACCC
CCAACCTGGTGGCCGCCCTGCCCCCCAGCACCCATGGGGCAGGTTGGCAGCTGTTTTGCAGGACTGTGTGGTCAGCACACTC
GGGGCCTACACGGATGGCCACAGCCATCGCCCGCTGCGCCCCAGATGAGGAGCTGCTGAGCTGCTCCAGTTTCTCCAGGAGT
GGGAAGCGGCGGGGCGAGCGCATGGAGGCCCAAGGGGGCAAGCTGGTCTGCCGGGCCCACAACGCTTTTGGGGGTGAGGGTG
TCTACGCCATTGCCAGGTGCTGCCTGCTACCCCAGGCCAACTGCAGCGTCCACACAGCTCCACCAGCTGAGGCCAGCATGGG
GACCCGTGTCCACTGCCACCAACAGGGCCACGTCCTCACAGGCTGCAGCTCCCACTGGGAGGTGGAGGACCTTGGCACCCAC
AAGCCGCCTGTGCTGAGGCCACGAGGTCAGCCCAACCAGTGCGTGGGCCACAGGGAGGCCAGCATCCACGCTTCCTGCTGCC
ATGCCCCAGGTCTGGAATGCAAAGTCAAGGAGCATGGAATCCCGGCCCCTCAGGAGCAGGTGACCGTGGCCTGCGAGGAGGG
CTGGACCCTGACTGGCTGCAGTGCCCTCCCTGGGACCTCCCACGTCCTGGGGGCCTACGCCGTAGACAACACGTGTGTAGTC
AGGAGCCGGGACGTCAGCACTACAGGCAGCACCAGCGAAGAGGCCGTGACAGCCGTTGCCATCTGCTGCCGGAGCCGGCACC
TGGCGCAGGCCTCCCAGGAGCTCCAGACC*GGTAAGCCTATCCCTAACCCTCTCCTCGGTCTCGATTCTACGGGAGGA*AATATG
GCTGATTGTTTTGGAGTTGTGATGGGAGTGATAGTGGTTGGCATTGTCATCCTGATCTTCACTGGGATCAGAGATCGGAAG
AAGAAAAATAAAGCAAGAAGTGGAGAAAATCCTTATGCCTCCATCGATATTAGCAAAGGAGAAAATAATCCAGGATTCCAAA
ACACTGATGATGTTCAGACCTCCTTTTAG

MGTVSSRRSWWPLPLLLLLLLLGPAGARAQEDEDGDYEELVLALRSEEDGLAEAPEHGTTATFHRCAKDPWRLPGTYVVVL
KEETHLSQSERTARRLQAQAARRGYLTKILHVFHGLLPGFLVKMSGDLLELALKLPHVDYIEEDSSVFAQSIPWNLERITPP
RYRADEYQPPDGGSLVEVYLLDTSIQSDHREIEGRVMVTDFENVPEEDGTRFHRQASKCDSHGTHLAGVVSGRDAGVAKGAS
MRSLRVLNCQGKGTVSGTLIGLEFIRKSQLVQPVGPLVVLLPLAGGYSRVLNAACQRLARAGVVLVTAAGNFRDDACLYSPA
SAPEVITVGATNAQDQPVTLGTLGTNFGRCVDLFAPGEDIIGASSDCSTCFVSQSGTSQAAAHVAGIAAMMLSAEPELTLAE
LRQRLIHFSAKDVINEAWFPEDQRVLTPNLVAALPPSTHGAGWQLFCRTVWSAHSGPTRMATAIARCAPDEELLSCSSFSRS
GKRRGERMEAQGGKLVCRAHNAFGGEGVYAIARCCLLPQANCSVHTAPPAEASMGTRVHCHQQGHVLTGCSSHWEVEDLGTH
KPPVLRPRGQPNQCVGHREASIHASCCHAPGLECKVKEHGIPAPQEQVTVACEEGWTLTGCSALPGTSHVLGAYAVDNTCVV
RSRDVSTTGSTSEEAVTAVAICCRSRHLAQASQELQ*TGKPIPNPLLGLDST*GGIWLIVFGVVMGVIVVGIVILIFTGIRDRK
KKNKARSGENPYASIDISKGENNPGFQNTDDVQTSF

C. Human PCSK9 TM-CT Lamp1

ATGGGCACCGTCAGCTCCAGGCGGTCCTGGTGGCCGCTGCCACTGCTGCTGCTGCTGCTGCTCCTGGGTCCCGCGGGCG
CCCGTGCGCAGGAGGACGAGGACGGCGACTACGAGGAGCTGGTGCTAGCCTTGCGTTCCGAGGAGGACGGCCTGGCCGAAGC
ACCCGAGCACGGAACCACAGCCACCTTCCACCGCTGCGCCAAGGATCCGTGGAGGTTGCCTGGCACCTACGTGGTGGTGCTG
AAGGAGGAGACCCACCTCTCGCAGTCAGAGCGCACTGCCCGCCGCCTGCAGGCCCAGGCTGCCCGCCGGGGATACCTCACCA
AGATCCTGCATGTCTTCCATGGCCTTCTTCCTGGCTTCCTGGTGAAGATGAGTGGCGACCTGCTGGAGCTGGCCTTGAAGTT
GCCCCATGTCGACTACATCGAGGAGGACTCCTCTGTCTTTGCCCAGAGCATCCCGTGGAACCTGGAGCGGATTACCCCTCCA
CGGTACCGGGCGGATGAATACCAGCCCCCCGACGGAGGCAGCCTGGTGGAGGTGTATCTCCTAGACACCAGCATACAGAGTG
ACCACCGGGAAATCGAGGGCAGGGTCATGGTCACCGACTTCGAGAATGTGCCCGAGGAGGACGGGACCCGCTTCCACAGACA
GGCCAGCAAGTGTGACAGTCATGGCACCCACCTGGCAGGGGTGGTCAGCGGCCGGGATGCCGGCGTGGCCAAGGGTGCCGGC
ATGCGCAGCCTGCGCGTGCTCAACTGCCAAGGGAAGGGCACGGTTAGCGGCACCCTCATAGGCCTGGAGTTTATTCGGAAAA
GCCAGCTGGTCCAGCCTGTGGGGCCACTGGTGGTGCTGCTGCCCCTGGCGGGTGGGTACAGCCGCGTCCTCAACGCCGCCTG
CCAGCGCCTGGCGAGGGCTGGGGTCGTGCTGGTCACCGCTGCCGGCAACTTCCGAGACGATGCCTGCCTCTACTCCCCAGCC
TCAGCTCCCGAGGTCATCACAGTTGGGGGCCACCAATGCCCAGGACCAGCCGGTGACCCTGGGGACTTTGGGGACCAACTTTG
GCCGCTGTGTGGACCTCTTTGCCCCAGGGGAGGACATCATTGGTGCCTCCAGCGACTGCAGCACCTGCTTTGTGTCACAGAG
TGGGACATCACAGGCTGCTGCCCACGTGGCTGGCATTGCAGCCATGATGCTGTCTGCCGAGCCGGAGCTCACCCTGGCCGAG
TTGAGGCAGAGACTGATCCACTTCTCTGCCAAAGATGTCATCAATGAGGCCTGGTTCCCTGAGGACCAGCGGGTACTGACCC
CCAACCTGGTGGCCGCCCTGCCCCCCAGCACCCATGGGGCAGGTTGGCAGCTGTTTTGCAGGACTGTGTGGTCAGCACACTC
GGGGCCTACACGGATGGCCACAGCCATCGCCCGCTGCGCCCCAGATGAGGAGCTGCTGAGCTGCTCCAGTTTCTCCAGGAGT
GGGAAGCGGCGGGGCGAGCGCATGGAGGCCCAAGGGGGCAAGCTGGTCTGCCGGGCCCACAACGCTTTTGGGGGTGAGGGTG
TCTACGCCATTGCCAGGTGCTGCCTGCCTCCCCAGGCCAACTGCAGCGTCCACACAGCTCCACCAGCTGAGGCCAGCATGGG
GACCCGTGTCCACTGCCACCAACAGGGCCACGTCCTCACAGGCTGCAGCTCCCACTGGGAGGTGGAGGACCTTGGCACCCAC
AAGCCGCCTGTGCTGAGGCCACGAGGTCAGCCCAACCAGTGCGTGGGCCACAGGGAGGCCAGCATCCACGCTTCCTGCTGCC
ATGCCCCAGGTCTGGAATGCAAAGTCAAGGAGCATGGAATCCCGGCCCCTCAGGAGCAGGTGACCGTGGCCTGCGAGGAGGG
CTGGACCCTGACTGGCTGCAGTGCCCTCCCTGGGACCTCCCACGTCCTGGGGGCCTACGCCGTAGCAACACGTGTGTAGTC
AGGAGCCGGGACGTCAGCACTACAGGCAGCACCAGCGAAGAGGCCGTGACAGCCGTTGCCATCTGCTGCCGGAGCCGGCACC
TGGCGCAGGCCTCCCAGGAGCTCCAGACC*GGTAAGCCTATCCCTAACCCTCTCCTCGGTCTCGATTCTACGGGAGGA*CTGAT
CCCCATCGCTGTGGGTGGTGCCCTGGCGGGGCTGGTCCTCATCGTCCTCATCGCCTACCTCGTCGGCAGGAAGAGGAGTCAC
GCAGGCTACCAGACTATCTAG

MGTVSSRRSWWPLPLLLLLLLLGPAGARAQEDEDGDYEELVLALRSEEDGLAEAPEHGTTATFHRCAKDPWRLPGTYVVVL
KEETHLSQSERTARRLQAQAARRGYLTKILHVFHGLLPGFLVKMSGDLLELALKLPHVDYIEEDSSVFAQSIPWNLERITPP
RYRADEYQPPDGGSLVEVYLLDTSIQSDHREIEGRVMVTDFENVPEEDGTRFHRQASKCDSHGTHLAGVVSGRDAGVAKGAG
MRSLRVLNCQGKGTVSGTLIGLEFIRKSQLVQPVGPLVVLLPLAGGYSRVLNAACQRLARAGVVLVTAAGNFRDDACLYSPA
SAPEVITVGATNAQDQPVTLGTLGTNFGRCVDLFAPGEDIIGASSDCSTCFVSQSGTSQAAAHVAGIAAMMLSAEPELTLAE
LRQRLIHFSAKDVINEAWFPEDQRVLTPNLVAALPPSTHGAGWQLFCRTVWSAHSGPTRMATAIARCAPDEELLSCSSFSRS
GKRRGERMEAQGGKLVCRAHNAFGGEGVYAIARCCLLPQANCSVHTAPPAEASMGTRVHCHQQGHVLTGCSSHWEVEDLGTH
KPPVLRPRGQPNQCVGHREASIHASCCHAPGLECKVKEHGIPAPQEQVTVACEEGWTLTGCSALPGTSHVLGAYAVDNTCVV
RSRDVSTTGSTSEEAVTAVAICCRSRHLAQASQELQ*TGKPIPNPLLGLDS*TGGLIPIAVGGALAGLVLIVLIAYLVGRKRSH
AGYQTI

METHODS OF REDUCING A VIRAL INFECTION AND KITS THEREFORE

CROSS REFERENCE TO RELATED APPLICATIONS

This application claims priority on U.S. provisional application Ser. No. 60/974,106, filed on Sep. 21, 2007. The document above is incorporated herein in its entirety by reference.

FIELD OF THE INVENTION

The present invention relates to methods of reducing a viral infection and kits therefore.

BACKGROUND OF THE INVENTION

Viruses and Membrane Host Cell Interactions

The emergence and re-emergence of infectious diseases is a direct consequence of increases in air travel, the worldwide intensification of farming and husbandry and global warming. Enveloped viruses (e.g., Human immunodeficiency virus (HIV), hepatitis C virus (HCV), Influenza virus, SARS coronavirus and West Nile virus) typically contain one or more membrane bound glycoproteins responsible for viral attachment and membrane fusion. In some cases both receptor binding and fusion properties are contained in the same molecule (e.g., influenza virus hemagglutinin), while in others these functions are mediated by two different glycoproteins (e.g., members of the alphavirus family). Despite differences in replication strategy among virus families, some basic principles are common between families. For example, analogous mechanisms govern virus entry into cells and the use of enzymes which direct the replication of the virus genome. At the progressed phase of adsorption the virions are engulfed into endocytic vesicles and the virion fusion domain(s) become(s) activated. Such activation can be accomplished by a conformational change, which occurs at acid pH and/or after protease-specific cleavage, resulting in fusion of viral and host-cell membranes. During penetration of the host cell, the viral membrane, via its surface/spike glycoprotein, fuses with either the plasma or endosomal membranes resulting in the release of the viral genome into the cytosol of infected cells. Membranes also play a crucial role in viral assembly, budding and cell-to-cell spreading of several virus families.

The Hepatitis C virus

The Hepatitis C virus (HCV) is a worldwide leading cause of chronic hepatitis, cirrhosis and hepatocellular carcinoma (45). This disease afflicts approximately 170 million people worldwide. The vast majority (80%) of HCV-infected patients fail to clear the infection and go on to develop liver associated-diseases. This is especially relevant since ~70% of chronic HCV infected individuals go on to develop hepatocellular carcinomas (HCC) and ~35% of HIV infected individuals in Europe and the USA have a hepatitis C co-infection. Additionally, with the introduction of highly active antiretroviral therapy for treatment of HIV, liver disease caused by chronic hepatitis C virus infection has now become an increasingly important cause of morbidity and mortality among HIV-infected patients. Therefore, treatment strategies for management of hepatitis C are urgently needed.

HCV is a positive strand RNA enveloped virus classified as a Hepacivirus within the Flaviviridae family (47). The RNA genome is ~9.6 kb in length and produces a single polyprotein of 3010-3040 amino acids that is processed by a combination of viral and cellular proteases, giving rise to at least 10 individual proteins (48).

In the absence of a prophylactic vaccine or a specific antiviral agent, the best treatment currently available for HCV infection is the combination therapy of peg-interferon and ribavirin (46) with which response to treatment has significantly improved therapy. However these treatments cause severe side effects, such as nausea, loss of appetite and mental depression.

The Human Immunodeficiency Virus

Human immunodeficiency virus type-1 (HIV-1) egress from infected cells is thought to be via assembly and budding at the plasma membrane and may involve components of the secretory apparatus, including tetraspanins. The HIV-1 envelope glycoprotein (Env) and the core protein (Gag) co-localize strongly with CD63 and CD81 and less strongly with CD9. It has been proposed that HIV-1 promotes virus assembly, budding and cell-cell transfer in T cells by targeting plasma membrane tetraspanin-enriched membrane domains (TEMs)(65). Tetraspanins such as CD63, CD81, and CD82, the lysosomal marker Lamp1, and the major histocompatibility complex II (MHC class II) molecules were associated with the budding virion compartment and were also shown to be present within the virion (65).

The Tetraspanin Superfamily

CD81 is a member of the tetraspanin superfamily which is composed of 33 highly hydrophobic small transmembrane proteins (tetraspanin proteins) that can form complexes in cholesterol-rich microdomains (also referred to as tetraspanin-enriched microdomains, TERM or TEM), distinct from lipid rafts, on the cell surface in a dynamic and reversible way (66). Through a multitude of homotypic and heterotypic interactions, tetraspanins regulate lateral clustering that can have effects on cellular adhesion and motility, interactions with stroma or affect signaling by growth factors, and for most of them no ligand has been identified. Data is also available for some tumors, where some tetraspanins have been identified as metastasis suppressors, but their significance is still not clear (66). In addition, certain tetraspanins function as viral co-receptors and may be important for viral egress from infected cells. It has recently become apparent that in addition to their purely structural function as organizers of TERM, tetraspanins also regulate various aspects of trafficking and biosynthetic processing of associated receptors (67).

Antiviral Strategies

Several strategies have been employed in the development of antiviral therapeutics. The most commonly used approaches include: 1) inhibitors of enzymes involved in the synthesis of viral DNA/RNA, 2) molecules including antibodies and receptor analogues that block viral/host cell interactions, 3) N-linked glycosylation inhibitors, 4) molecules which modulate viral capsid assembly/disassembly, 5) inhibitors of viral and host proteases required for the maturation of viral proteins/glycoproteins, and 6) molecules that block membrane fusion.

Many of the actual and prospective candidates will likely succumb to ensuing drug resistance owing to the high rates of mutation typical of several viruses. New drugs which can respond to unmet medical needs are always beneficial.

In order to develop new antiviral compounds, there is a need to identify novel cellular target genes having an antiviral activity.

The present description refers to a number of documents, the content of which is herein incorporated by reference in their entirety.

SUMMARY OF THE INVENTION

The present invention relates to the surprising identification of proprotein convertase subtilisin/kexin type 9 preproprotein (PCSK9) as a novel anti-viral target or compound. The present invention relates to methods of treating a vertebrate, particularly a mammal and more particularly murine or human patient, suffering from one or more viral infections, or a cell infected with one or more viral infections, said viral infections including but not limited to infections of the following viruses: hepatitis C, HIV, hepatitis A, hepatitis B, hepatitis E, and hepatitis G, or other viruses by administering to said patient infected with at least one virus an activator of the PCSK9 activity.

Results presented herein clearly indicate that Huh7 cells constitutively expressing PCSK9 wild type are unable to sustain efficient viral replication. The effect was even more pronounced when using PCSK9 chimeras harbouring an increased activity on LDLR (co-pending application PCT/CA2007/000794 filed May 8, 2007 in the name of Seidah). As exemplified in FIG. 1, one of the chimeras used herein contains the trans-membrane and the cytosolic domains of the protein ACE2 fused to the carboxy terminal end of PCSK9 wild type amino acid sequence. The expression of such chimeric protein leads to a marked reduction of the LDLR at the surface of Huh7 cells. Interestingly, the construct clears completely HuH7 cells from viral RNA as observed following infection. Cells overexpressing PCSK9-ACE2 and, to a lesser extent PCSK9 wild type, had a marked reduction in the number of colony forming unit (CFU) when compared to control Huh7 cultures. A reduction in the number of CFU is also observed in cultures treated with purified recombinant PCSK9 when added directly to the culture supernatant. Taking together these data show that PCSK9 plays an inhibitory role on viral infection by HCV.

More specifically, the Applicants identified PCSK9 as a novel liver-specific viruses target that could be used for the development of compounds having antiviral activity. More specifically, the antiviral activity could be against HCV. The treatment of liver cells with compounds leading to the activation of endogenous PCSK9 activity or which mimic the PCSK9 activity is thus desirable for the treatment of HCV infection.

The Applicants thus identified PCSK9 as a novel target for the regulation of tetraspanin proteins at the cell surface. More specifically the tetraspanin protein at the cell surface could be CD81. A compound acting on the PCSK9 activity could thus find application in any CD81-associated diseases, including other viral infection (e.g., HCV and HIV-1) as well as non-viral CD81-associated diseases, such as cancer.

More specifically, in accordance with an aspect of the present invention there is provided a method for treating and/or preventing a proprotein convertase subtilisin/kexin type 9 preproprotein (PCSK9)-susceptible viral infection comprising increasing a PCSK9 activity and/or expression in a biological system infected by the virus, whereby the increased PCSK9 activity and/or expression treats and/or prevents the viral infection in the biological system.

In a specific embodiment, the PCSK9-susceptible viral infection is caused by an enveloped virus. In another specific embodiment, the enveloped virus is human immunodeficiency virus (HIV) or hepatitis C virus (HCV).

In accordance with another aspect of the present invention there is provided a method of modulating the expression of a cellular receptor involved in viral infection at the surface of cells in a biological system, comprising modulating a proprotein convertase subtilisin/kexin type 9 preproprotein (PCSK9) activity and/or expression in the cells, whereby the modulating of PCSK9 activity and/or expression modulates the expression of the cellular receptor at the surface of the cells.

In a specific embodiment, the cellular receptor is a tetraspanin. In another specific embodiment, the tetraspanin is CD81. In another specific embodiment, the method is for decreasing the expression of CD81 at the surface of cells, and wherein the biological system is susceptible for viral infection by hepatitis C virus (HCV) and/or human immunodeficiency virus (HIV), and comprises increasing a PCSK9 activity and/or expression in the cells, whereby the increasing of the PCSK9 activity and/or expression decreases the expression of the CD81 at the surface of the cells.

In another specific embodiment, the biological system susceptible for viral infection comprises hepatocytes or immune cells.

In accordance with a further aspect of the present invention there is provided a method of identifying an agent for treating and/or preventing proprotein convertase subtilisin/kexin type 9 preproprotein (PCSK9)-susceptible viral infection comprising: (a) selecting a test compound able to increase PCSK9 activity and/or expression; and (b) assaying the ability of the compound to reduce (i) the PCSK9-susceptible viral infection in a biological system in vitro; and/or (ii) CD81 expression at the surface of cells in the biological system in vitro, wherein the ability of the compound to increase PCSK9 activity and/or expression, and to reduce (i) and/or (ii) is an indication that the test compound can treat and/or prevent the PCSK9-dependent viral infection.

In accordance with still a further aspect of the present invention there is provided a method of identifying a virus, the viral infection of which is treatable and/or preventable by a proprotein convertase subtilisin/kexin type 9 preproprotein (PCSK9) activity and/or expression, comprising: (a) infecting a biological system that expresses PCSK9 with the virus, wherein a lower level of infection in the biological system that expresses the PCSK9 than that in the biological system that does not express the PCSK9 is an indication that the viral infection is treatable and/or preventable by a PCSK9 activity and/or expression.

In a specific embodiment, the viral infection is a liver-specific viral infection. In another specific embodiment, the biological system is cells, a tissue, or an organ. In another specific embodiment, the PCSK9 activity is increased by a PCSK9 polypeptide or a fragment thereof. In another specific embodiment, the increasing of the PCSK9 activity and/or expression in the biological system comprises an increase of PCSK9 secretion. In another specific embodiment, the biological system is a human subject.

In accordance with another aspect of the present invention there is provided a method of evaluating the susceptibility of a subject to a viral infection comprising (i) measuring the concentration of soluble proprotein convertase subtilisin/kexin type 9 preproprotein (PCSK9) in a blood sample of the subject; or (ii) determining whether the subject expresses a PCKS9 variant associated with a low or complete PCSK9 loss of function; or (iii) a combination of (i) and (ii), wherein a lower amount of soluble PCSK9 in the blood sample of the subject than that in a control sample and/or a determination that the subject expresses the PCSK9 variant, is an indication that the subject is susceptible to a viral infection.

In accordance with still a further aspect of the present invention there is provided a method of classifying a subject having a viral infection comprising (i) measuring the concentration of soluble proprotein convertase subtilisin/kexin type 9 preproprotein (PCSK9) in a blood sample of the subject; or (ii) determining whether the subject expresses a PCKS9 variant associated with a low or complete PCSK9 loss of function; or (iii) a combination of (i) and (ii), wherein the result of the measuring step and/or of the determining step enables the classification of the subject into a subgroup.

In accordance with still a further aspect of the present invention there is provided a method of selecting a treatment for a subject having a viral infection comprising (i) measuring the concentration of soluble proprotein convertase subtilisin/kexin type 9 preproprotein (PCSK9) in a blood sample of the subject; or (ii) determining whether the subject expresses a PCKS9 variant associated with a low or complete PCSK9 loss of function; or (iii) a combination of (i) and (ii), wherein a concentration of the soluble PCSK9 lower in the blood sample of the subject than that in a control blood sample and/or a determination that the subject expresses the PCSK9 variant, is an indication that a PCSK9 activator may be a useful treatment for the subject.

In accordance with still a further aspect of the present invention there is provided a method of evaluating the efficacy of a treatment against a viral infection in a treated subject, comprising measuring the concentration of soluble proprotein convertase subtilisin/kexin type 9 preproprotein (PCSK9) in a blood sample of the subject, wherein a concentration of soluble PCSK9 higher in the blood sample of the subject than that in a control blood sample, is an indication that the treatment is efficient.

In a specific embodiment, the viral infection is a human immunodeficiency virus (HIV) infection or a hepatitis C virus (HCV) infection.

In accordance with still a further aspect of the present invention there is provided a kit comprising a proprotein convertase subtilisin/kexin type 9 preproprotein (PCSK9) activator, and at least one other therapeutic agent against a viral infection and/or instructions to use the activator for treating the viral infection.

In accordance to another aspect of the present invention, there is provided a method of measuring the level of circulating PCSK9, with specific assays, to evaluate the efficacy of a compound to up regulate PCSK9 in infected patients (co pending application PCT/CA2007/000794 filed May 8, 2007 in the name of Seidah). In specific embodiment, the infected patient is infected by HCV. In another specific embodiment, the infected patient is infected by HIV.

The level of PCSK9 in plasma collected from patients is measured by known techniques such as an enzyme-linked immunosorbant assay (ELISA), immunoprecipitation followed by Western blotting and quantitative mass spectrometry.

Co pending application PCT/CA2007/000794 filed May 8, 2007 in the name of Seidah shows that human PCSK9 is cleaved by furin/PC5 into a secretable C-terminal fraction lacking the first 218 amino acids and designated PCSK9-$\Delta N_{218}$ (219-692) in that application. It also showed that in all cases, PCSK9 (full length PCSK9 form extending from amino acids 153 to 692) and its PCSK9-$\Delta N_{218}$ product are both circulating in male and female plasma. The total amount of soluble PCSK9 forms as well as the ratio between these two circulating forms varies between individuals.

The total level of all soluble PCSK9 forms present in plasma collected from patients with PCSK9-associated viral infections are measured by known techniques such as an enzyme-linked immunosorbant assay (ELISA), immunoprecipitation followed by Western blotting and quantitative mass spectrometry. The in-house polyclonal human antibody (Ab1-hPC9) recognizes both full-length and cleaved forms, whereas the in house monoclonal antibody only recognizes the furin/PC5-cleaved C-terminal PCSK9 form. An antibody that specifically binds to the full-length can be produced by using the 153-218 fragment as antigen (or any species equivalent e.g., monkey 153-218, etc.). The combined use of both antibodies, in ELISA for example, allows the determination of the full-length to furin/PC5-cleaved PCSK9 forms ratio. The furin/PC5-cleaved PCSK9 form was measured to represent from 10 to 20% of total PCSK9 forms in a normal sample. These measurements are used as a diagnostic tool for the tailor-made therapeutic approach applicable to each patient.

The present invention provides a method of measuring the total amount of PCSK9 (all soluble forms) and the use of such measurements as a diagnostic tool in PCSK9-associated viral infections. Commercially available antibodies include rabbit anti-human PCSK9-(490-502) pAb (Cayman Chemical, catalog no. 10007185) which recognizes pro-PCSK9 and PCSK9-N218 but not full-length form of PCSK9 (amino acids 153-692) and goat anti-human PCSK9 (679-692) (Imgenex, catalog no IMX-3786) antibodies.

The above-mentioned methods may also be used for classifying or stratifying a subject into a subgroup (based on PCSK9 expression and/or activity, or expression of a PCSK9 variant associated with a low or complete PCSK9 loss of function for example, or a combination of PCSK9 expression and/or activity with that of another viral infection susceptibility marker associated with viral infection) having different phenotypes enables a better characterization of viral infections and eventually a better selection of treatment depending on the subgroup to which the subject belongs. For instance, a subgroup of subject expressing no PCSK9 or expressing a PCSK9 variant associated with a low or complete PCSK9 loss of function, may be appropriately treated by providing them compounds (e.g., a PCSK9 fragment) having the PCSK9 activity while a subgroup of subjects expressing a low amount of PCSK9 could also be appropriately treated with an agent increasing expression and/or activity of PCSK9.

As used herein, a substantially similar level refers to a difference in the level of expression or activity between the level determined in a first sample (i.e. test sample) and the reference level which is about 10% or less; in a further embodiment, 5% or less; in a further embodiment, 2% or less.

As used herein, a "higher" or "increased" level refers to a level of expression or activity in a sample (i.e. test sample) which is at least 15% higher, in an embodiment at least 25% higher, in a further embodiment at least 40% higher; in a further embodiment at least 50% higher, in a further embodiment at least 100% higher (i.e. 2-fold), in a further embodiment at least 200% higher (i.e. 3-fold), in a further embodiment at least 300% higher (i.e. 4-fold), relative to the reference level (e.g., in the presence of a PCSK9 activator).

As used herein, a "lower" or "decreased" level refers to a level of expression or activity in a sample (i.e. test sample) which is at least 15% lower, in an embodiment at least 25% lower, in a further embodiment at least 40% lower; in a further embodiment at least 50% lower, in a further embodiment at least 100% lower (i.e. 2-fold), in a further embodiment at least 200% lower (i.e. 3-fold), in a further embodiment at least 300% lower (i.e. 4-fold), relative to the reference level.

A "subject in need thereof" or a "patient" in the context of the present invention is intended to include any subject that will benefit or that is likely to benefit from the increase in the expression or activity of PCSK9. In an embodiment, a subject in need thereof is a subject diagnosed with an viral infection having a lower PCSK9 expression or activity or expresses a PCSK9 variant associated with a low or complete PCSK9 loss of function.

A "reference" or "control" level may be determined, for example, by measuring the level of expression of PCSK9 nucleic acid or encoded polypeptide, or the level of PCSK9 activity, in a corresponding biological sample obtained from one or more control subject(s) (e.g., not suffering from a viral infection, or not treated against a viral infection). When such a control level is used, a lower or decreased level measured in a biological sample (i.e. test sample) is indicative for example that the PCSK9 inhibitor may be useful for treating or preventing a viral infection.

In accordance to another aspect of the present invention, there is provided a method of evaluating the presence of PCSK9 variants in the genomic sequence of an infected patient in order to evaluate the efficacy of a compound for treating the infected patient.

DEFINITION

As used herein the term "envelope virus families" refers to viruses having a phospholipid bilayer membrane derived from the host cell that contains cellular and viral protein. This class of virus includes but is not restricted to HIV, hepatitis C(HCV), HBV, SARS, influenza and Ebola.

As used herein the terms "soluble PCSK9" and "soluble PCSK9 forms" are used interchangeably and refer to all soluble PCSK9 forms including full-length 153-692 and PCSK9-$\Delta N_{218}$.

As used herein the term "PCSK9-susceptible viral infection" refers to, without being so limited, liver-specific viruses and HIV.

As used herein the term "liver-specific viruses" refers to viruses able to replicate in the liver and include but is not restricted to hepatitis A virus (HAV), hepatitis B virus (HBV), hepatitis C virus (HCV), hepatitis delta virus (HDV) hepatitis E virus, hepatitis G virus (HGV), and the torque teno virus (TTV).

As used herein the term "tetraspanin" refers to a superfamily of small, four transmembrane domain proteins that are involved in very diverse physiological processes. Members of tetraspanin include but are not restricted to CD9, CD37, CD53, CD63, CD81 and CD82.

Point mutations in the PCSK9 gene within its coding exons (31) are associated with either familial hypercholesterolemia (32-36) or hypocholesterolemia (37-39) phenotypes. It was suggested that some PCSK9 single point mutations result in a gain or enhanced function of PCSK9 on the degradation of LDLR in acidic compartments, possibly endosomes (6;11), while others would cause a loss of function (37), and these would be associated with the development of hyper- or hypo-cholesterolemia, respectively (38;40). It was thus hypothesized that high levels of active PCSK9 are associated with a faster rate of degradation of the cell surface LDLR, resulting in increased amounts of circulating LDL-cholesterol, as the uptake of the latter in liver hepatocytes by the LDLR will be diminished accordingly, and vice versa. This would suggest that the level of cell surface LDLR is inversely proportional to the level of hepatic and likely intestinal active PCSK9. This hypothesis is reinforced by the in vivo observations that in mice lacking a functional PCSK9 gene (PCSK9-knockout mice), the level of hepatocyte cell surface LDLR is greatly enhanced resulting in an ~50% drop in the level of circulating LDL-cholesterol (41), whereas mice overexpressing PCSK9 result in higher levels of circulating LDL-cholesterol (6;9;10; 42). As used herein, the term "PCSK9 variant associated with a low or complete PCSK9 loss of function" thus refers to a PCSK9 having one or more mutations decreasing its ability to reduce viral infection (e.g., by decreasing its ability to reduce the level of cellular receptor involved in viral infection at the cell surface). Such variants are described for instance in Table 1 of co-pending PCT/CA2007/000794 filed May 8, 2007 in the name of Seidah et al. Without being so limited, such cellular receptor includes LDLR and tetraspanins such as CD81.

As used herein the term "PCSK9 activity" refers to detectable enzymatic, biochemical or cellular activity attributable to PCSK9. Without being so limited, such activities include PCSK9 secretion, the effect of PCSK9 on reducing the level of low density lipoprotein receptor (LDLR), very low density lipoprotein receptor (VLDLR) (Official Symbol: VLDLR and Entry gene ID: 7436, NCBI), apolipoprotein e receptor 2 (ApoER2) (Official Symbol: LRP8 and Entry gene ID: 7804, NCBI), low density lipoprotein receptor-related protein (LRP), or CD81 at the cell surface, as well as the reduction of viral replication.

Thus PCSK9 activity could also be indirectly measured by evaluating the level of expression of PCSK9 (or of a nucleic acid/polypeptide whose expression is modulated by PCSK9 activity), or a fragment thereof, in cells as well as in a biological sample (tissue, organ, fluid). PCSK9 expression levels could be determined at the polypeptide and/or nucleic acid levels using any standard methods known in the art (see below). PCSK9 activity could also be indirectly measured by evaluating the level of expression or activity of a reporter gene (e.g., luciferase, B-galactosidase, alkaline phosphatase, GFP) operably linked to a transcriptionally regulatory element normally associated with a PCSK9 gene or with a gene whose expression is modulated by PCSK9 activity.

By the "fragment of PCSK9" in the present context is meant to refer to any peptide fragment derived from the amino acid sequence of 1-692 amino acids of human PCSK9 for example, and variants thereof, or modified forms, capable of mimicking the activity of PCSK9. In an embodiment, the above-mentioned fragment is the soluble form of PCSK9 (e.g., full length 153-629).

Regulation of PCSK9 Expression or Activity

Without being so limited, increasing the PCSK9 activity and/or expression could be achieved by various mechanisms, which among others could act at the level of: (i) its transcription where its mRNA levels are upregulated by SREBP-2, and downregulated by cholesterol (26;27) via a reduced level of activated nuclear SREBP-2 (27;28), (ii) its translation which may be controlled by specific factors, (iii) its post-translational modifications including its zymogen cleavage and/or activation, glycosylation, sulfation (3;6), or possibly by other processing events resulting in its degradation (3), (iv) its cellular localization and/or sorting of mature PCSK9, (v) its level of secretion, and possibly, (vi) its subsequent cellular re-uptake. Alternatively, compounds such as peptides could mimic the activity of PCSK9.

PCSK9 expression levels could be determined using any standard methods known in the art. Non-limiting examples of such methods include Western blot, immunoblot, enzyme-linked immunosorbant assay (ELISA), radioimmunoassay (RIA), immunoprecipitation, immunocytochemistry, immunohistochemistry, as well as methods to determine mRNA levels such as RT-PCR and northern analysis, real-time PCR, PCR, in situ hybridization and so on.

PCSK9 Gene

As used herein the terms "PCSK9 gene" or "PCSK9" refers to genomic DNA encoding sequences comprising those sequences referred to in GenBank by GeneID number NM_174936.2. The description of the various aspects and embodiments of the invention is provided with reference to exemplary wild type PCSK9 nucleic acid sequence and amino acid sequence. Such reference is meant to be exemplary only and the various aspects and embodiments of the invention are also directed to other PCSK9 nucleic acids and polypeptides, such as PCSK9 nucleic acid or polypeptide mutants/variants, splice variants of PCSK9 nucleic acids, PCSK9 variants from species to species or subject to subject.

Processing of PCSK9

The human full-length PCSK9 (1-692) is cleaved into pro-protein PCSK9 (i.e. without signal peptide) (31-692) which can also be cleaved into active full-length PCSK9 ("active form") (153-692). Furin/PC5 could inactivate the PCSK9 active form by its cleavage into a N-terminal fragment ranging from amino acids 153 to 218 and a C-terminal fragment ranging from amino acids 219 to 692 (PCSK9-$\Delta N_{218}$).

As used herein, the term "PCSK9 modulator" refers to a compound that directly or indirectly increases or decreases the PCKS9 activity. It thus refers to any compound able to directly or indirectly increase or increase the transcription, translation, post-translational modification or activity of PCSK9. It includes intracellular as well as extracellular PCSK9 modulators including PCSK9 itself. Without being so limited, such modulators include RNA molecules, proteins, peptides, small molecules, antibodies, etc.

As used herein, the term "PCSK9 activator" refers to a compound that directly or indirectly increases the PCKS9 activity and/or expression. It thus refers for instance to any compound able to directly or indirectly increase the transcription, translation, post-translational modification or activity of PCSK9. It includes intracellular as well as extracellular PCSK9 activators including PCSK9 itself and a fragment thereof. Without being so limited, such activators include RNA molecules, proteins, peptides, small molecules, antibodies, etc.

As used herein, the term "PCSK9" or "PCSK9 fragment" refers to a PCSK9 polypeptide sequence having the ability to lower the protein level of CD81 or LDLR at the cell surface and/or to reduce viral infection. As used herein, it is not limited to the native PCSK9 sequence but encompasses any functional recombinant or mutant sequence, or chemically modified variants having preserved the ability to reduce the level of CD81 or LDLR at the cell surface and/or to reduce viral infection. Without being so limited, various PCSK9 polypeptide fragments are described in PCT/CA2007/000794 to Seidah.

Viral infections can be detected/quantified in any method known in the art including detection/measure of viral DNA and RNA, detection/measure of viral protein, and detection/measure of CFU.

In accordance with another aspect of the present invention, there is provided a purified PCSK9, or fragment thereof, having maintained an ability to reduce viral infection.

As used herein the term "purified" in the expression "purified polypeptide" means altered "by the hand of man" from its natural state (i.e. if it occurs in nature, it has been changed or removed from its original environment) or it has been synthesized in a non-natural environment (e.g., artificially synthesized). Use of these terms does not refer to absolute purity (such as a homogeneous preparation) but instead represents an indication that it is relatively more pure than in the natural environment. For example, a protein/peptide naturally present in a living organism is not "purified", but the same protein separated (about 90-95% pure at least) from the coexisting materials of its natural state is "purified" as this term is employed herein.

Similarly, as used herein, the term "purified" in the expression "purified antibody" is simply meant to distinguish man-made antibody from an antibody that may naturally be produced by an animal against its own antigens. Hence, raw serum and hybridoma culture medium containing anti-PCSK9-$\Delta N_{218}$ antibody are "purified antibodies" within the meaning of the present invention.

As used herein, the term "ligand" broadly refers to natural, synthetic or semi-synthetic molecules. The term "molecule" therefore denotes for example chemicals, macromolecules, cell or tissue extracts (from plants or animals) and the like. Non limiting examples of molecules include nucleic acid molecules, peptides, antibodies, carbohydrates and pharmaceutical agents. The ligand appropriate for the present invention can be selected and screened by a variety of means including random screening, rational selection and by rational design using for example protein or ligand modeling methods such as computer modeling. The terms "rationally selected" or "rationally designed" are meant to define compounds which have been chosen based on the configuration of interacting domains of the present invention. As will be understood by the person of ordinary skill, macromolecules having non-naturally occurring modifications are also within the scope of the term "ligand". For example, peptidomimetics, well known in the pharmaceutical industry and generally referred to as peptide analogs can be generated by modeling as mentioned above.

Antibodies

As used herein, the term "PCSK9 antibody" or "immunologically specific anti-PCSK9 antibody" refers to an antibody that specifically binds to (interacts with) a PCSK9 protein and displays no substantial binding to other naturally occurring proteins other than the ones sharing the same antigenic determinants as the PCSK9. The term antibody or immunoglobulin is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')$_2$, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$—$V_H$), anticalins, Pep-Bodies™, antibody-T-cell epitope fusions (Troybodies) or Peptibodies. Additionally, any secondary antibodies, either monoclonal or polyclonal, directed to the first antibodies would also be included within the scope of this invention. Commercially available antibodies include rabbit anti-human PCSK9-(490-502) pAb (Cayman Chemical, catalog no. 10007185) which recognizes pro-PCSK9 and PCSK9-N218 but not full-length form of PCSK9 (amino acids 153-692) and goat anti-human PCSK9 (679-692) (Imgenex, catalog no IMX-3786) antibodies.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g., Fab and Fab' fragments) which inhibit or neutralize their respective interaction domains in Hyphen and/or are specific thereto.

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen, immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to ⅒ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293 (see also, e.g., Lindenbaum et al., 2004).

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell (see, e.g., Goding 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

As used herein, the term "a" or "the" means "at least one".

As used herein the term "subject" is meant to refer to any mammal including human, mice, rat, dog, cat, pig, cow, monkey, horse, etc. In a particular embodiment, it refers to a human.

As used herein the terminology "biological sample" refers to any solid or liquid sample isolated from a living being. In a particular embodiment, it refers to any solid or liquid sample isolated from a human. Without being so limited it includes a biopsy material, blood, saliva, synovial fluid, urine, amniotic fluid and cerebrospinal fluid.

As used herein the terminology "blood sample" is meant to refer to blood, plasma or serum.

As used herein the terms "control sample" and "control blood sample" are meant to refer to a sample from a subject known not to suffer from viral infection under scrutiny in the assay. In specific embodiments, it is the sample of a subject known not to suffer from a viral infection. In particular embodiments where a HCV or HIV viral infection is under scrutiny, it thus refers to a sample from a subject known not to suffer from HCV or HIV.

In a specific embodiment, the control sample (e.g., control blood sample) is selected from a sample from the subject at an earlier stage of the disease or disorder or before the subject had the disease. In another embodiment, the control sample is from a different subject that does not have the disease or disorder or predisposition to develop the disease or condition.

In another specific embodiment, the subject is pre-diagnosed with the disease or condition. For instance, the suspect may be known to be HIV positive.

In another specific embodiment, the subject is suspected of having the disease.

Agents and Pharmaceutical Compositions

In another aspect, the present invention provides an agent that modulates the expression and/or activity of PCSK9 for preventing and/or treating a viral infection. Such an agent may be, for example (i) a PCSK9 polypeptide or fragment thereof; (ii) an antibody (e.g., polyclonal or monoclonal), natural or artificial variants, or antibody fragments, which specifically binds to PCSK9 and promotes its activity; (iii) a small molecule or peptide that promotes the activity and/or expression of PCSK9.

The invention also provides a pharmaceutical composition (medicament) comprising at least one agent of the invention (e.g., an agent that increases the expression and/or activity of PCSK9), and a pharmaceutically acceptable diluent, carrier, salt or adjuvant. Such carriers include, for example, saline, buffered saline, dextrose, water, glycerol, ethanol, and combinations thereof. The pharmaceutical composition may be adapted for the desired route of administration (e.g., oral, parental, intravenous, intramuscular, intraperitoneal and aerosol).

The invention also provides pharmaceutical compositions which comprise one or more agent(s) modulating PCKS9 activity. Typically, the activity of PCSK9 is increased. The invention also provides pharmaceutical compositions which comprise one or more agent(s) modulating PCSK9 activity and/or expression in combination with another anti-viral agent. In a specific embodiment, the present invention thus also encompasses using a combination of a PCSK9 activator with at least another therapeutic agent known to reduce liver-specific viral infections including interferon, peg-interferon, ribavirin, lamivudine, adefovir dipivoxil, entecavir and telbivudine or HIV such as HIV protease inhibitors (i.e. amprenavir, indinavir, saquinavir, lopinavir), HIV reverse transcriptase inhibitors (i.e. nucleoside analog 3TC, lamivudine AZT (zidovudine)) and fusion inhibitors (i.e. enfuvirtide).

Dosage

The amount of the agent or pharmaceutical composition which is effective in the prevention and/or treatment of a particular disease, disorder or condition (e.g., viral infection) will depend on the nature and severity of the disease, the chosen prophylactic/therapeutic regimen (i.e., compound, DNA construct, protein, cells), the target site of action, the subject's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a subject, in the context of the present invention should be sufficient to effect a beneficial prophylactic and/or therapeutic response in the subject over time. The size of the dose also will be determined by the existence, nature, and extent of any adverse side-effects that accompany the administration. Effective doses may also be extrapolated from dose response curves derived from in vitro or animal model test systems.

The terms "treat/treating/treatment" and "prevent/preventing/prevention" as used herein, refer to eliciting the desired biological response, i.e., a therapeutic and prophylactic effect, respectively. In accordance with the subject invention, the therapeutic effect comprises one or more of a decrease/reduction in viral infection (e.g., reduced/decreased viral replication and/or spreading of viruses), a decrease/reduction in the severity or number of the viral infection symptoms, an amelioration of symptoms and viral infection effects, and an increased survival time of the affected subject, following administration of the agent/composition of the invention. In accordance with the invention, a prophylactic effect may comprise a complete or partial avoidance/inhibition/blocking or a delay of viral infection development/progression (including a complete or partial avoidance/inhibition or a delay of viral infection development), and an increased survival time of the affected subject, following administration of the agent that increase PCSK9 expression and/or activity (or of a composition comprising the agent).

As such, a "therapeutically effective" or "prophylactically effective" amount of an agent capable of increasing the expression and/or activity of PCSK9, or a combination of such agents, may be administered to a subject, in the context of the methods of treatment and prevention, respectively, described herein.

Kits

The present invention also provides a kit or package comprising the above-mentioned agent or pharmaceutical compositions. Such kit may further comprise, for example, instructions for the prevention or treatment of a viral infection, containers, devices for administering the agent/composition, etc.

The present invention also relates to a kit comprising one or more compounds, isolated/purified nucleic acid, isolated/purified protein and/or isolated/purified ligand such as an antibody in accordance with the present invention. For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the subject sample (DNA genomic nucleic acid, cell sample or blood samples), a container which contains in some kits of the present invention, the probes used in the methods of the present invention, containers which contain enzymes, containers which contain wash reagents, and containers which contain the reagents used to detect the extension products. Kits of the present invention may also contain instructions to use these compounds, isolated nucleic acid, probes, ligands and or antibodies in the methods of the present invention.

Screening Assays

Given the correlation between PCSK9 expression/activity and viral infectivity, compounds which are capable of increasing PCSK9 expression/activity may be used for the reduction of viral infection. Therefore, the invention further relates to screening methods for the identification and characterization of compounds capable of increasing PCSK9 expression and/or activity, which may be used for the prevention and/or treatment of viral infection.

The present invention also provides a method (e.g., an in vitro method) for determining whether a test compound is useful for the prevention and/or treatment of a viral infection, said method comprising: (a) contacting said test compound with a PCSK9 polypeptide, or a fragment thereof or variant thereof having PCSK9 activity; and (b) determining the activity of the PCSK9 polypeptide, fragment or variant thereof, in the presence or absence of said test compound; wherein an increase in the activity of PCSK9 in the presence of said test compound relative to the absence thereof is indicative that said test compound may be used for the prevention and/or treatment of the viral infection.

The present invention also provides a method (e.g., an in vitro method) for determining whether a test compound is useful for the prevention and/or treatment of a viral infection, said method comprising: (a) contacting said test compound with a cell expressing PCSK9; and (b) determining the expression and/or activity of PCSK9 in the presence or absence of said test compound; wherein an increase in the expression and/or activity of PCSK9 in the presence of said test compound relative to the absence thereof is indicative that said test compound may be used for the prevention and/or treatment of the viral infection.

The present invention also provides a method (e.g., an in vitro method) for determining whether a test compound is useful for the prevention and/or treatment of a viral infection, said method comprising: (a) contacting said test compound with a cell comprising a first nucleic acid comprising a transcriptionally regulatory element normally associated with a PCSK9 gene, operably linked to a second nucleic acid comprising a reporter gene encoding a reporter protein; and (b) determining whether the reporter gene expression and/or reporter protein activity is increased in the presence of said test compound; wherein said increase in reporter gene expression and/or reporter protein activity is indicative that said test compound may be used for prevention and/or treatment of the viral infection.

Other objects, advantages and features of the present invention will become more apparent upon reading of the following non-restrictive description of specific embodiments thereof, given by way of example only with reference to the accompanying drawings.

Figure 2:
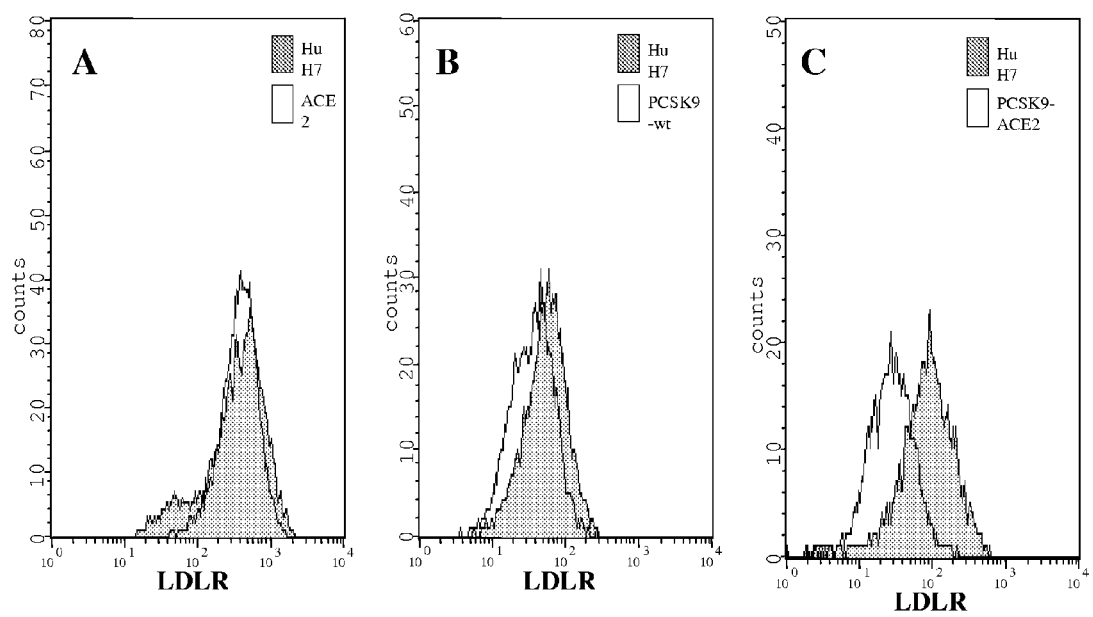
Figure 3:
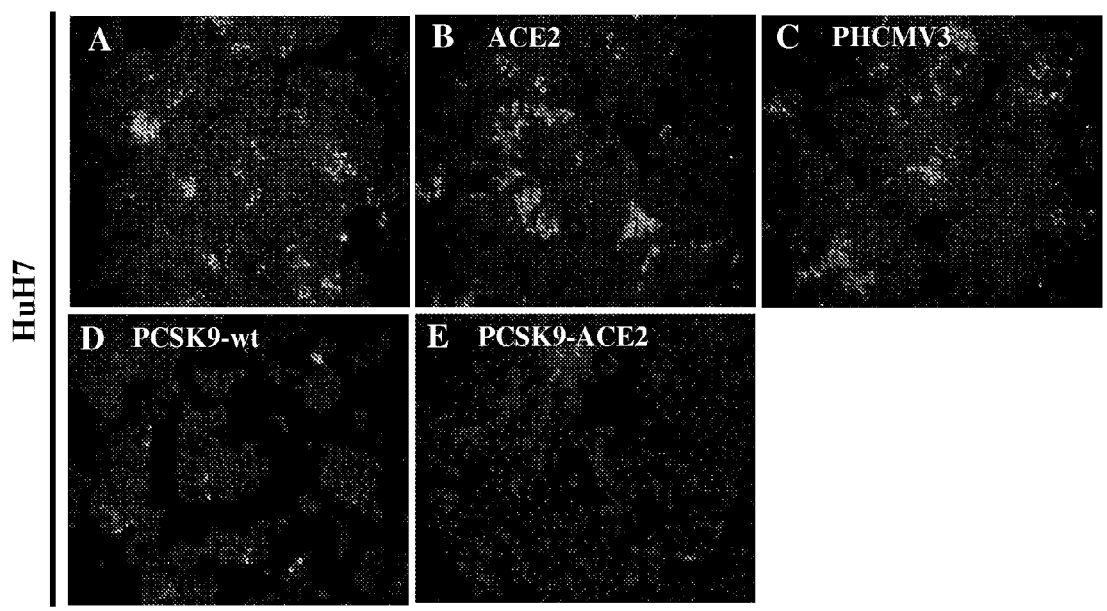
Figure 4:
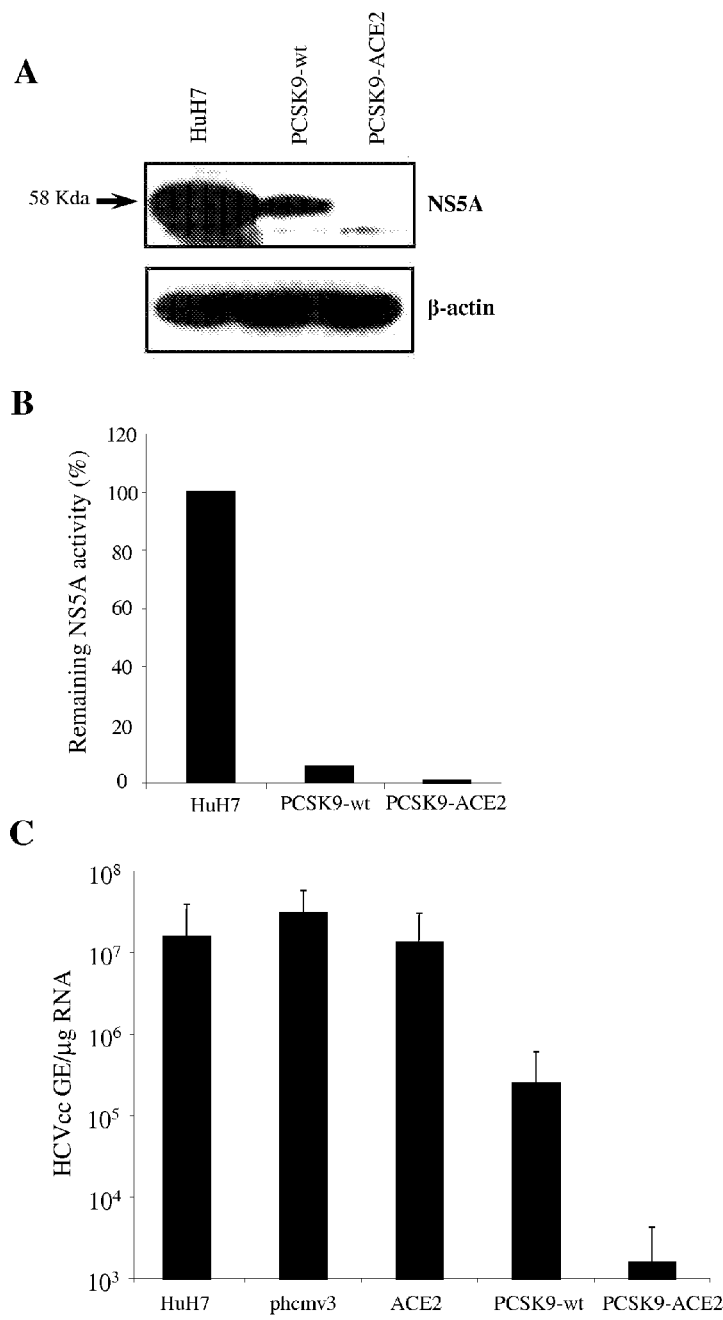
Figure 5:
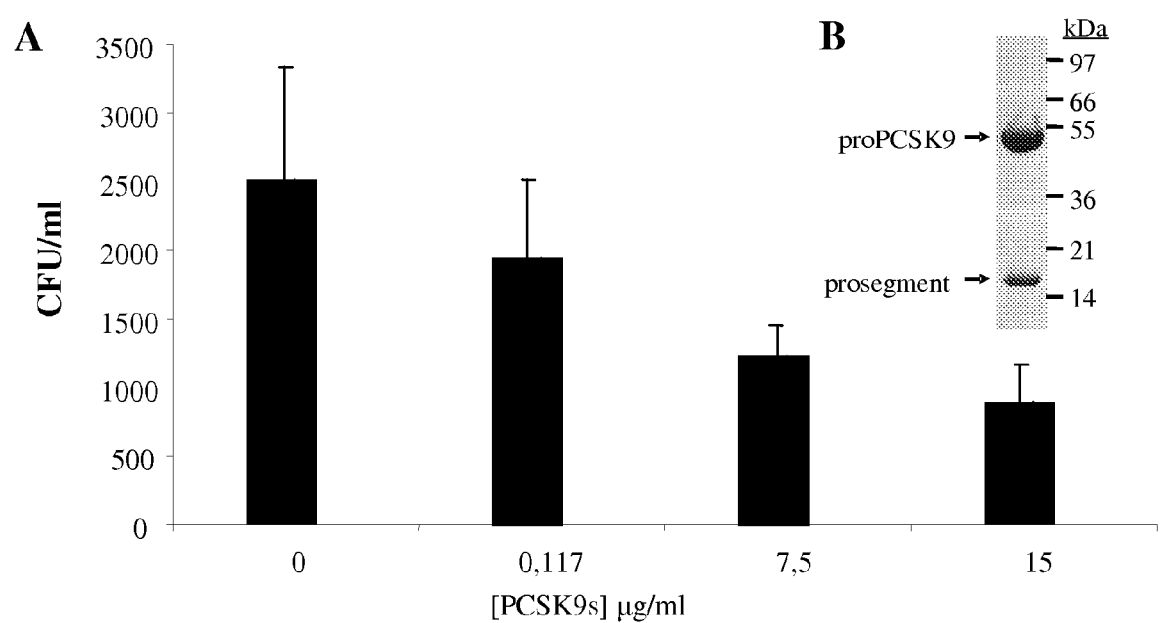
Figure 6:
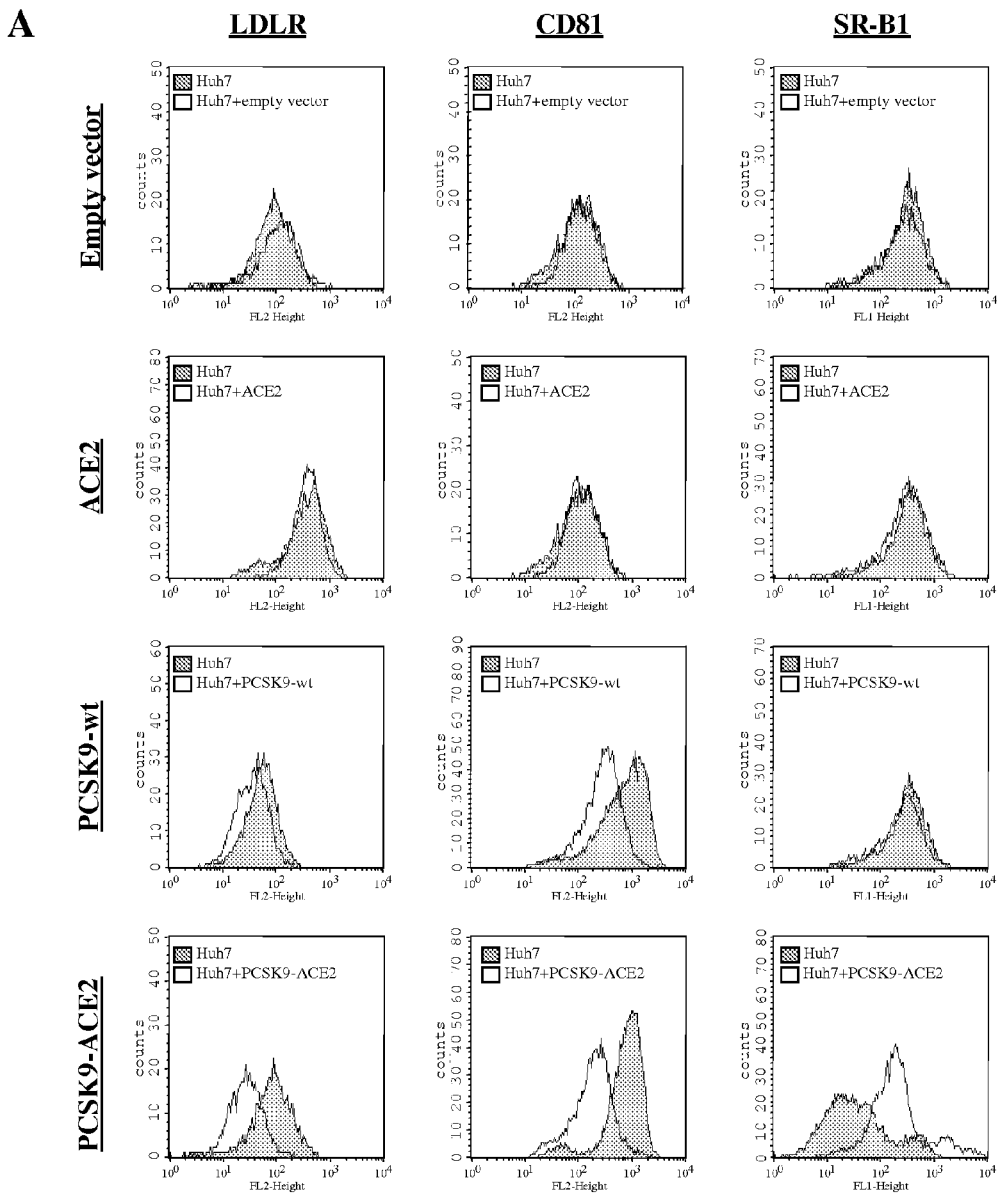
Figure 7:
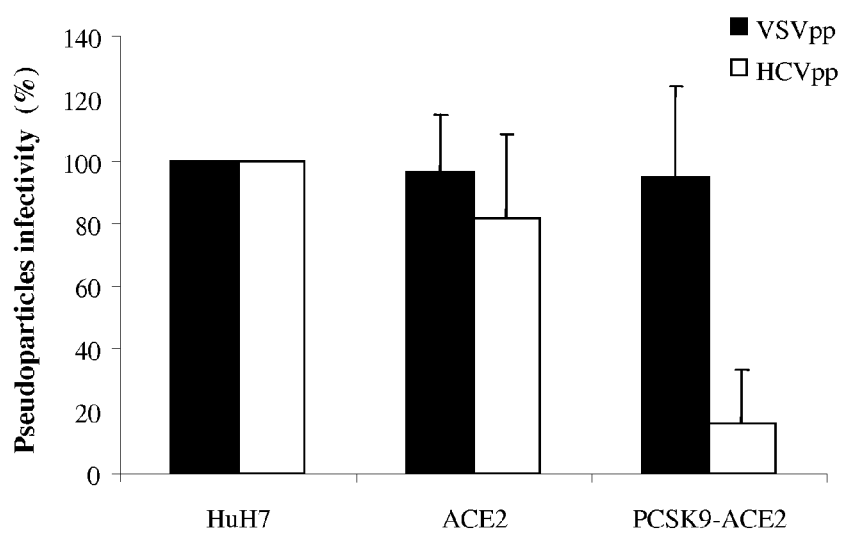
Figure 8:
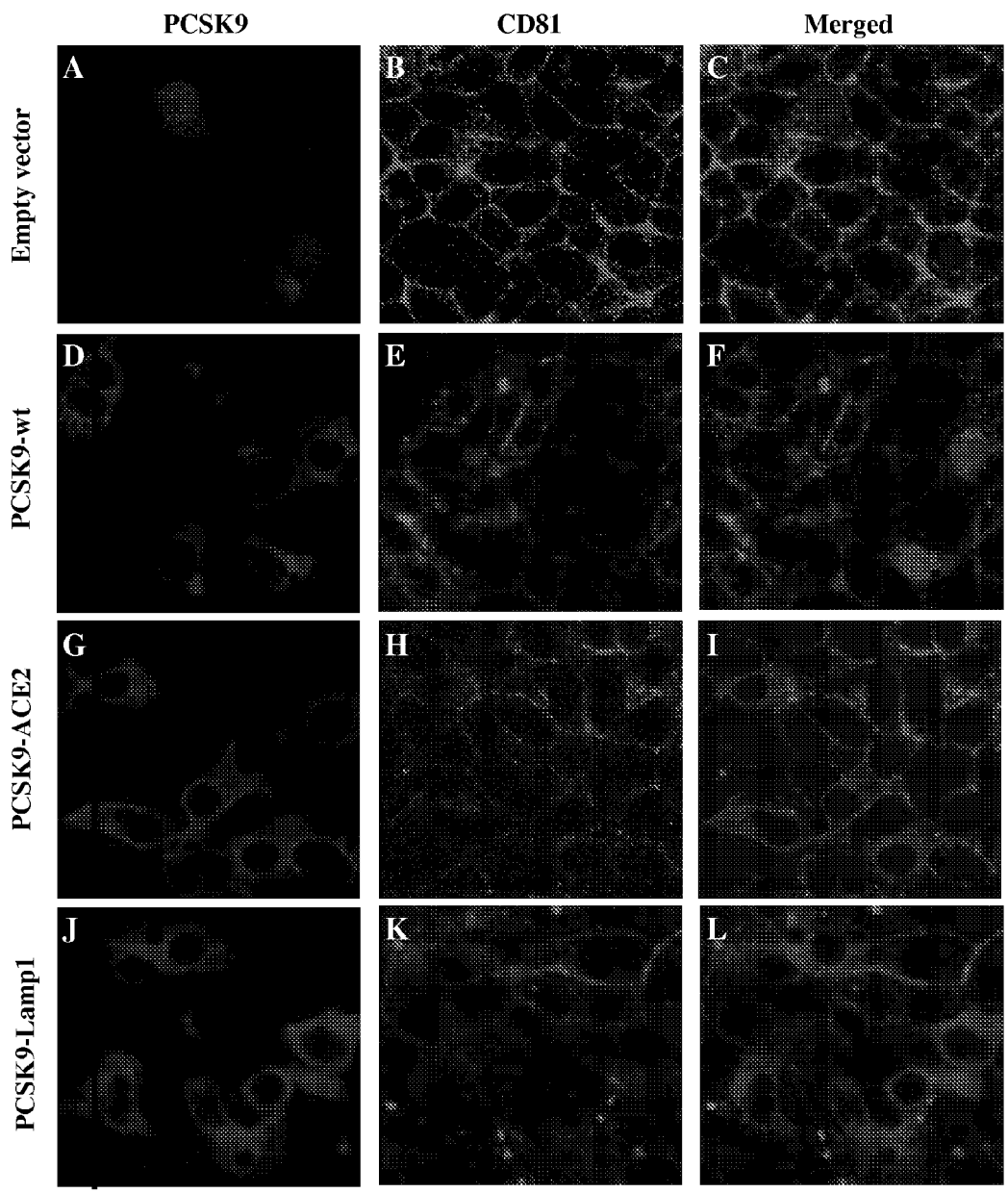
Figure 9:
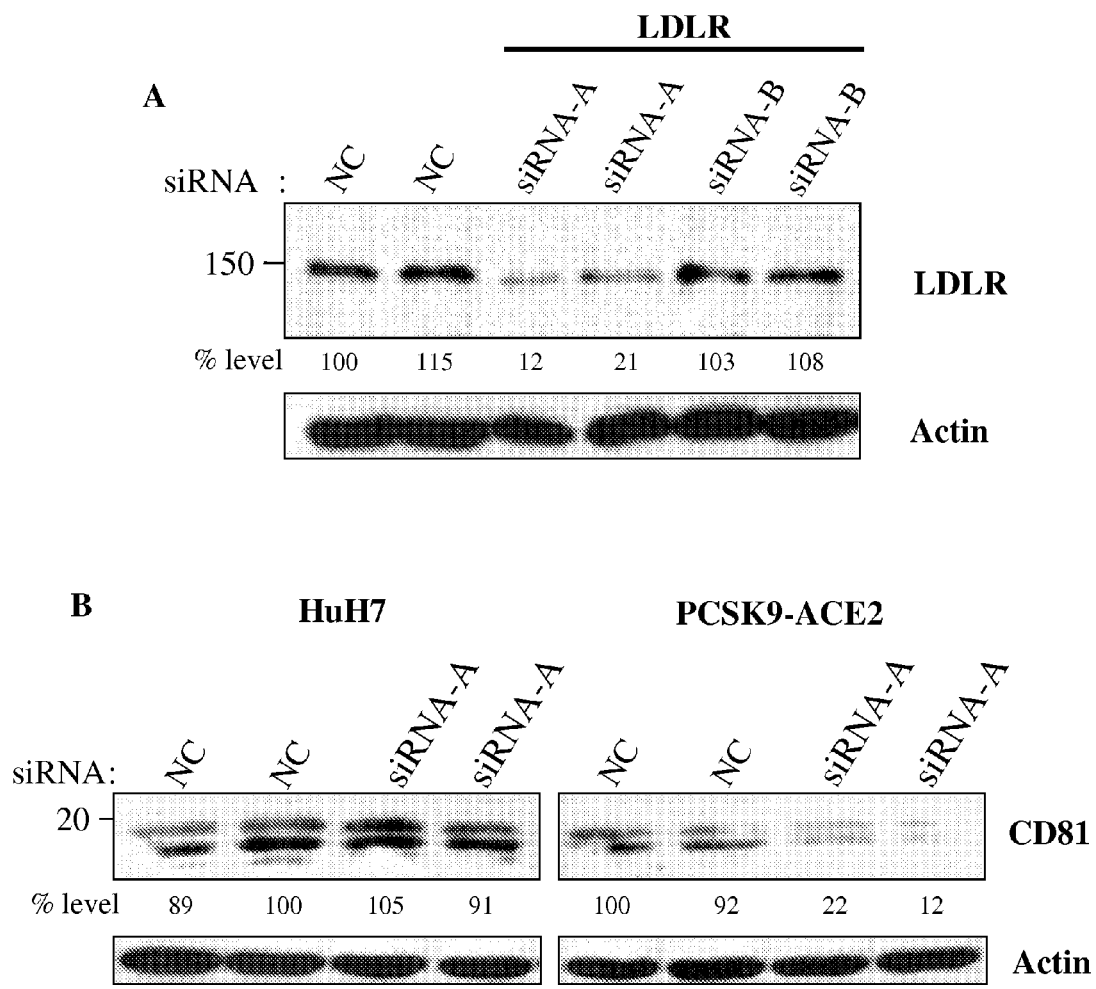
Figure 10:
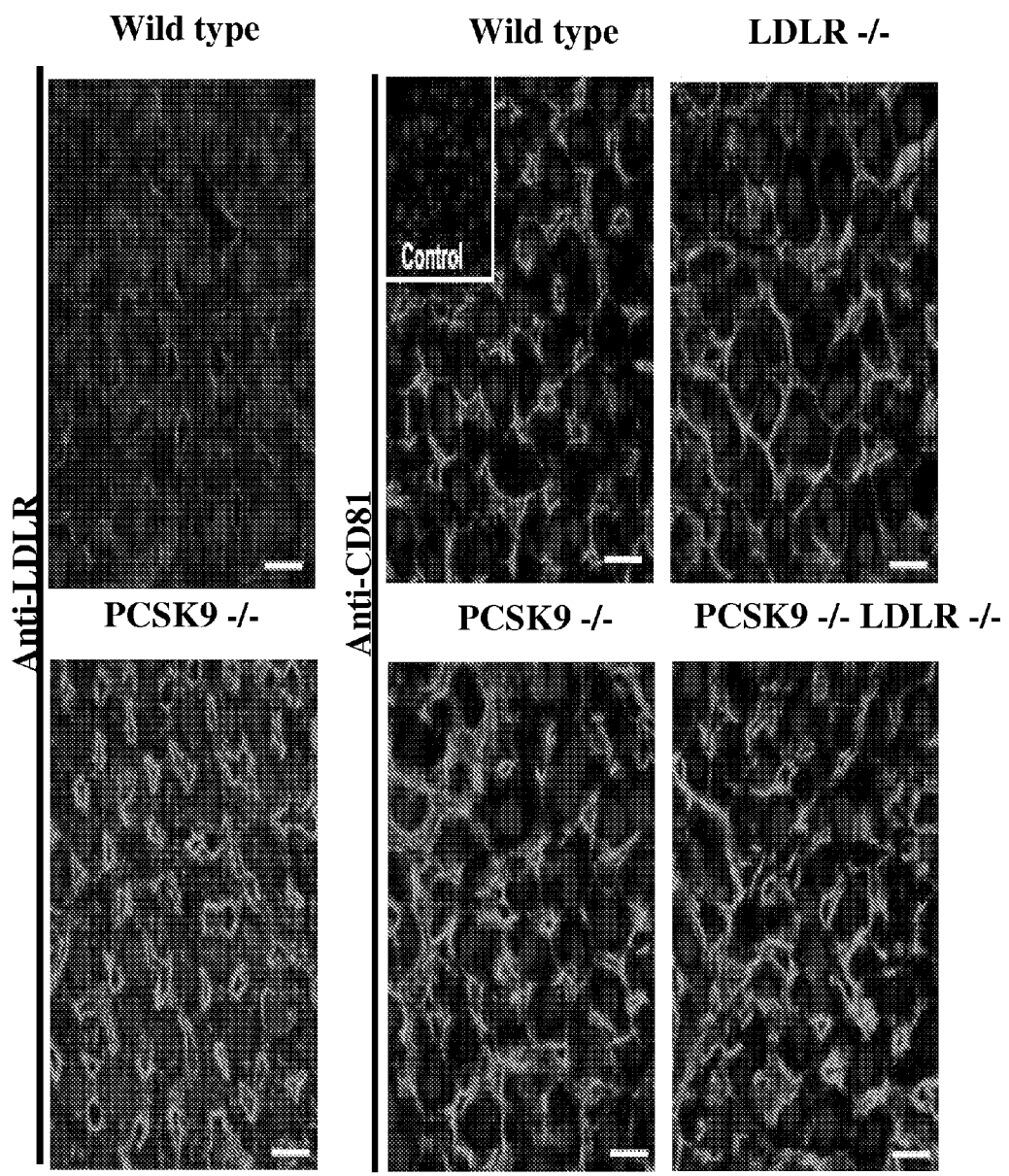

(B) shows a representative view of a cell sorting of PCSK9-ACE2 positive cells, whereupon the 10% higher expressors were collected. (C) Western blots showing the levels of stably expressed PCSK9-wt, PCSK9-ACE2 or ACE2 in HuH7 cells. The antibodies used were: Ab1-hPC9 for PCSK9 and C-18 for ACE2. (D) FACS analysis of PCSK9-wt and PCSK9-ACE2 cell surface expression on HuH7 cells. (E) Confocal microscope analysis of the immunofluorescence staining of PCSK9-wt and PCSK9-ACE2 protein in HuH7 cells using Ab1-hPC9;

FIG. 2 shows cell surface expression of LDLR on HuH7 cells expressing: (A) ACE2, (B) PCSK9-wt, or (C) PCSK9-ACE2. These are representative data for at least two independent experiments;

FIG. 3 shows the effect of PCSK9 expression in HuH7 cells on resistance to cell-culture adapted hepatitis C virus (HCVcc) infection. It presents immunofluorescence showing foci of HCVcc infected cells at 72 h post-infection. Colonies were visualized by immunostaining of the NS5A protein (palest dots) and the nuclei were stained with DAPI. Stable cell lines expressing: (A) mock transfected, (B) ACE2, (C) phcmv3 (empty plasmid), (D) PCSK9-wt and (E) PCSK9-ACE2;

FIG. 4 shows the effect of PCSK9 and PCSK9-ACE2 in stably transfected Huh7 cells on blocking the infection by HCV. HuH7 cells were infected with JFH-1 for 15 days. (A) Western blotting showing the HCV NS5A protein and β-actin in the infected cells. (B) Quantification of the remaining NS5A protein expression in the infected HuH7 cells, calculated from the blot in A. Infected normal HuH7 cells were arbitrarily set as 100% and the NS5A expression level were normalized with the chemiluminescence of β-actin. (C) Intracellular JFH-1 RNA was calculated by quantitative RT-PCR (Taqman). Input RNAs were normalized by the quantification of the ribosomal RNA 18S;

FIG. 5 shows the effect of purified soluble PCSK9 into the culture media on infection of cells by HCVcc strain JFH1. (A) HuH7 cells were plated and treated with purified soluble human PCSK9 (0 to 15 μg/ml) for 4 h prior to infection with J6/JFH1. At 3 days post-infection, HCV NS5A protein was stained with a rabbit polyclonal antibody. The activity of soluble PCSK9 was calculated from the colony forming units (CFU) observed in the treated HuH7 cells as compared to mock control. These are representative data of two independent experiments performed in duplicate. (B) Purity of soluble recombinant PCSK9 was attested by Coomassie blue staining;

FIG. 6 shows the effect of the expression of PCSK9 and PCSK9-ACE2 on HCV receptors expression at the cell surface. Cell surface expression of LDLR, CD81 and SR-BI was analyzed by FACS using monoclonal antibodies for the detection of LDLR and CD81 (left and center panels, respectively) and a polyclonal antibody for the detection of SR-BI (right panels). These are representative data of at least three independent experiments;

FIG. 7 shows the effect of PCSK9 expression on HCV pseudo-particles (HCVpp) infection. Naïve HuH7, or stable HuH7 ACE2 and HuH7 PCSK9-ACE2 cells were infected with HCVpp or vesicular stomatitis virus pseudo-particles (VSVpp) for 72 h. Luciferase activity (RLU) was calculated 72 h post-infection, and pseudoparticles infectivity was calculated relative to the infection of HuH7 cells by HCVpp, arbitrarily set at 100%. VSVpp infections were used as positive controls. The values are the average of five independent experiments;

FIG. 8 shows the effect of PCSK9 expression on CD81 expression on HuH7 cells. PCSK9 and CD81 expression analyzed by immunocytochemistry on a confocal microscope. HuH7 cells were transiently transfected with cDNAs coding for an empty vector, PCSK9-wt, PCSK9-ACE2 or PCSK9-Lamp1. HuH7 cells expressing (A,B,C) pIRES plasmid, (D,E,F) PCSK9-wt, (G,H,I) PCSK9-ACE2, and (J,K,L) PCSK9-Lamp1;

FIG. 9 shows whether CD81 reduction by PCSK9 is LDLR independent. (A) HuH7 cells were transfected in duplicate with a non-specific siRNA as negative control (NC) or siRNAs directed against LDLR (siRNA-A and siRNA-B). Expression of the target proteins was verified 48 h post-transfection by Western blotting using an LDLR antibody. (B) HuH7 and PCSK9-ACE2 cells were transfected with siRNA-NC or siRNA-A. Expression of CD81 was verified 48 h post-transfection by Western blotting using the monoclonal antibody 5A6. Percentages represent the remaining expression of the proteins after normalization to β-actin;

FIG. 10 shows the CD81 expression in the liver of Pcsk9 and Ldlr KO mice. LDLR and CD81 expression were analyzed by immunohistochemistry (green) in liver cryosections of wild type, single KO [Pcsk9$^{-/-}$] and double KO [Pcsk9$^{-/-}$ Ldlr$^{-/-}$] mice. For each condition at least 10 fields were compared. These experiments were repeated 2 times. Nuclei were stained with TO-PRO-3 (blue). Bars=20 μm; and FIG. 11 shows A) the cDNA nucleotide (SEQ ID NO: 1) and amino acid (SEQ ID NO: 2) sequences of full length human PCSK9-WT (1-692). The fragment fused to the C-terminal end of the PCSK9 is a V5-tag (italicized); B) the cDNA nucleotide (SEQ ID NO: 3) and amino acid (SEQ ID NO: 4) sequences of full length human PCSK9 fused to the transmembrane and the cytosolic domains (TM-CT) of ACE2. TM-CT underlined. The fragment between the PCSK9 1-692 and the TM-CT is a V5-tag (italicized); and C) the cDNA nucleotide (SEQ ID NO: 5) and amino acid (SEQ ID NO: 6) sequences of full length human PCSK9 (1-692) fused to the transmembrane and the cytosolic domains (TM-CT) of Lamp1. TM-CT underlined. The fragment between the PCSK9 1-692 and the TM-CT is a V5-tag (italicized).

DESCRIPTION OF ILLUSTRATIVE EMBODIMENTS

The present invention is illustrated in further details by the following non-limiting examples presenting the identification of novel functionally-relevant protein functions and assays measuring theirs activities.

EXAMPLE 1

Material and Methods

Cells and Virus—HuH7 and HEK293T cells were maintained in Dulbecco's modified Eagle medium high glucose (DMEM) (Invitrogen) supplemented with 5 mM sodium pyruvate, 100 U of penicillin/ml, 100 μg of streptomycin/ml, and 10% fetal calf serum. All cells were grown at 37° C. in 5% $CO_2$. The HCVcc JFH-1 and J6/JFH1 were obtained from Dr T. Wakita and R. Bartenschlager, respectively, and were propagated as described (69, 71).

Plasmids and Stable Cell Lines—HuH7 cell populations expressing PCSK9, PCSK9-TM-CT-ACE2 (PCSK9-ACE2), PCSK9-TM-CT-Lamp1 (PCSK9-Lamp1), ACE2 or the empty phCMV3 vector (Invitrogen) were generated as described (72).

The PCSK9 sequence used is shown on FIG. 11A and included a V5-tag (italicized in FIG. 11A); the PCSK9-ACE2 sequence used is shown on FIG. 11B and contained the transmembrane and the cytosolic domains of the protein ACE2 (underlined in FIG. 11B) fused to the carboxy terminal end of PCSK9 wild type sequence including a V5-tag (italicized in FIG. 11B); the PCSK9-Lamp1 sequence used is shown on FIG. 11C and contained the trans-membrane and the cytosolic domains of the protein LAMP1 (underlined in FIG. 11C) fused to the carboxy terminal end of PCSK9 wild type sequence including a V5-tag (italicized in FIG. 11C); and the ACE2 sequence used is shown on FIG. 11D.

HuH7 cells were transfected with 2 µg of the corresponding plasmid using Lipofectamine™ 2000 (Invitrogen) as described by the manufacturer. At 24 h post-transfection, G418 (800 µg/ml) was added to the cultured media for stable selection of transfected cells. Once the selection was completed, PCSK9 and PCSK9-ACE2 cells were sorted by FACS using a rabbit polyclonal anti-PCSK9 antibody (Ab1-hPC9) (70). The ~10% higher expressors were isolated and used for further experimentations. All stable cell lines were cultured under selective pressure by the addition of 600 µg/ml of G418 to the media.

Quantitative RT-PCR (Taqman)—Total cellular RNA was extracted and purified with Trizol™ as described by the manufacturer (Invitrogen). The cDNAs were prepared from 250 ng of total RNA. Briefly, RNAs were incubated for 3 min at 70° C. then cooled on ice for 2 min before the addition of 4 µl of RT-Buffer 5× (Invitrogen), 2 µl DTT (0.1 M), 1 µl random primer p (dN6) (100 ng/µl), 1 µl dNTP (20 mM), 20 U of RNAsin and 100 U of MMLV reverse-transcriptase. Samples were incubated for 10 min at 25° C. and 1 h at 37° C. To inactivate the MMLV, samples were incubated 15 min at 70° C. and the cDNAs diluted to a final volume of 200 µl with Rnase-free water. The primers used for amplification were: 5'UTR-R 5'-GAGTGGGTTTATCCAAGAAAG-3' (SEQ ID NO: 7) and 5'UTR-F: 5'-TCTGCGGAACCGGTGAGT-3' (SEQ ID NO: 8). The mixture consisted of 2.5 µl of cDNA in a final volume of 25 µl of reaction mixture containing 8.6 µl of $H_2O$, 0.5 µl of probe FAM-UTR (12, 5 pmole/µl) 5'-CG-GAATTGCCGGGAAGACTG-3' (SEQ ID NO: 9), 0.25 µl (90 pmole/µl) of each HCV primer. For internal control, the 18S Ribosomal RNA Kit was used as suggested by the manufacturer (Applied Biosystem). The mixture was completed with 12.5 µl of the Taqman Universal Master Mix™ 2× (Applied Biosystem) and the amplification was performed as suggested by the manufacturer in a Rotor-Gene RG-3000™ (Corbet Research).

Flow Cytometry—Cell surface expression of PCSK9, PCSK9-ACE2 and CD81 was monitored by recovering the cells using trypsin, 0.25% EDTA (Invitrogen). Approximately $1 \times 10^6$ cells were fixed in PBS containing 4% formaldehyde for 10 min and blocked in PBS 3% FBS for 30 min at 4° C. Cells were stained for 1 h at 4° C. with anti-PCSK9 (Ab1-hPC9) (70) or an anti-CD81 (Santa Cruz Biotechnology) antibody at a dilution of 1:200 and 1 µg/ml, respectively, in PBS 3% FBS. Cells were washed twice in PBS and incubated for 30 min at 4° C. with a rabbit-polyclonal-Alexa 488 antibody or mouse-specific secondary antibodies conjugated with phycoerythrin (PE) (1:1000) (Jackson ImmunoResearch) in PBS 3% FBS, respectively. For the detection of the SR-BI and LDLR at the cell surface, the cells were re-suspended in Versene™ and treated as for the detection of CD81, except that the primary antibody was an anti-SR-BI (Novus Bio) used at 1 µg/ml, an anti-LDLR (C7) (Santa Cruz Biotechnology) and the secondary antibody was a goat anti-rabbit-Alexa-488 (Molecular Probe) (1:1000) and an anti-mouse PE-conjugated (1:1000) (Jackson ImmunoResearch), respectively. All samples were analyzed immediately using a FACSCalibur™.

Indirect Immunofluorescence—HuH7 cells were seeded on cover glass ($2 \times 10^4$ cells per cover glass) and infected 24 h later with a concentrated virus J6/JFH1 (MOI 0.1). At 72 h post-infection, the cells were fixed with 4% paraformaldehyde in PBS. Staining of HCV NS5A was performed using polyclonal anti-NS5A (obtained from O Virochem) antibody for 1 h (dilution 1:200) in a solution of PBS containing 3% BSA, 10% FBS and 10% Triton™ X-100. Antibodies were washed 4× in PBS and bound antibodies were detected by incubation for 1 h with anti-rabbit goat Alexa 488 antibody at a dilution of 1:500. Unbound antibodies were washed 4× with PBS. The cells were then incubated with DAPI (dilution 1:36000) to stain the nuclei in blue. Immunofluorescence analysis was performed by counting manually the foci of infection (green fluorescence) with a Nikon™ microscope TE2000. Indirect immunofluorescence of PCSK9 and CD81 antigens was performed using a PCSK9 antibody (70) and a CD81 antibody, used at dilutions of 1:2000 and 1:200, respectively.

Western Blotting—The cells were seeded on 96-well plate at a density of $4 \times 10^4$ per well, 24 h before infection. Cells were then infected with HCVcc J6/JFH1 (MOI 0.1) for 12 days and then homogenized and washed 2× in PBS. Proteins homogenate of $2 \times 10^5$ cells were heated for 4 min at 95° C. before separation by SDS-PAGE. The resolved proteins were then electrophoretically transferred to an Immuno-Blot PVDF membrane for protein blotting (Bio-Rad) for 45 min. Non-specific binding sites were blocked for 1 h in PBS-5% skim milk and the membrane stained for 1 h. The antibodies used were rabbit polyclonal anti-NS5A (1:2000, obtained from O. Nicolas, Virochem), rabbit polyclonal anti-PCSK9 (1:2000, Ab1-hPC9) (70), goat polyclonal anti-ACE2 (1:200) (C-18 SantaCruz Biotechology). After incubation with the primary antibody, the membranes were washed 4× in PBS-0.1% Tween-20. Bound antibodies were detected by incubation for 45 min with a goat anti-rabbit HRP antibody (1:10000, Jackson Immunosearch) or a donkey anti-goat HRP antibody (1:10000, Jackson Immunosearch). The signals were developed with a SuperSignal™ West Pico chemiluminescent substrate (Pierce). The chemiluminescence of the NS5A was normalized to the internal control, β-actin, and recorded in real-time using the Chemigenius™ gel documentation system (Syngene).

For that purpose an anti-V5 epitope (1/3000)(Invitrogen), an anti-PCSK9 (1/1000) (Ab1-hPC9, NG. Seidah) or an anti-ACE2 (1/500) (Santa Cruz) were used. The proteins were revealed using the appropriate secondary HRP-conjugated antibodies with the SuperSignal™ West Pico chemiluminescent substrate (Pierce).

PCSK9 Inhibition Assay—HuH7 cells were seeded on a 96 well plate at a density of $8 \times 10^3$ cells per well 24 h before the addition of a serial dilution of purified human PCSK9 (range from 0 to 15 µg/ml) (a generous gift from R. Parker and F. J. Duclos, Bristol Myers Squibb, NJ). The cells were then infected with 50 µl of JFH-1 infectious supernatant after 6 h of incubation with graded amounts of purified PCSK9. Fresh PCSK9 and media were added daily and the infection was stopped at 72 h post-infection by fixing the cells in 4% formaldehyde in PBS. The cells were then immunostained with an NS5A antibody, as described above, and NS5A positive foci were visualized with a Nikon™ microscope TE2000.

HCV pseudoparticles production—To generate HCV pseudoparticles, HEK293T cells were transfected with expression vectors encoding E1E2 HCV glycoprotein and VSV pseudo-particles, generated by transfection of HEK293T cells with an expression vector encoding the glycoprotein of vesicular stomatitis virus. HEK293T cells were plated the day before transfection in a medium without antibiotic at a density of 2.5×10$^6$ cells in 10 cm plates. The next day, the gag-pol packaging construct (8 μg), the luciferase vector (8.1 μg) and the glycoprotein-expressing construct (3 μg) were transfected in HEK293T cells using a calcium phosphate transfection protocol (Promega transfection protocol) and incubated overnight. The next day, the media were replaced by a complete medium and 24 h later, they were filtered on a 0.45 μm membrane and stored at −80° C. For VSVpp generation, the same protocol was used except that 8 μg of gag-pol, 8.1 μg of luciferase and 2.7 μg of VSVG were transfected.

Pseudotyped Virus Infectivity Assays—HuH7 cells were seeded at a density of 4×10$^4$ cells/well in a 24-well plate and cultured overnight. The next day 500 μl of infectious HCVpp was added to the wells and the plate incubated overnight. The next day, the medium was replaced with fresh complete DMEM for 72 h. Cells were rinsed in PBS and trypsinized. Detached cells were centrifuged out and the pellet was stored at −80° C. Luciferase activity was determined using a Luciferase assay system (Promega).

LDLR siRNA Assay—For siRNA transfection experiments, HuH7 and HuH7 PCSK9-ACE2 cells were seeded at 1×10$^5$ cells/well in 24-well plates the day before. LDLR siRNAs (s224006; siRNA-A and s224007; siRNA-B) were purchased from Ambion and transfected using Lipofectamine™ 2000 (Invitrogen), according to the manufacturer's protocol. As negative control, a non-specific siRNA was used. Cells were trypsinized 48 h after transfection and LDLR expression was analyzed by Western blotting using a chicken polyclonal anti-LDLR antibody (1:3000) (Abcam) and a goat anti-chicken HRP secondary antibody (1:10000) (Abcam).

Immunohistochemistry—For CD81 visualization, frozen mouse liver sections were fixed and permeabilized in MeOH: acetone (1:1) for 3 min at −20° C. The cells were washed 3× for 2 min in PBS and blocked in 1% BSA for 30 min. CD81 was labelled with hamster anti-CD81 EAT2 antibody (1:20 Santa Cruz) overnight at 4° C. CD81 immunoreactivity was revealed with a goat anti-hamster IgG-FITC (1:50 eBioscience). Nuclei were stained with TO-PRO-3 Marker (blue; Invitrogen). For the detection of LDLR, a goat anti-mLDLR (1:100; R&D systems) and a donkey anti-goat-Alexa 488 (Invitrogen) were used. As control, the omission of the primary antibody demonstrated the specificity of the labelling.

EXAMPLE 2

PCSK9 Expression in Stable Cell Lines

Figure 1:
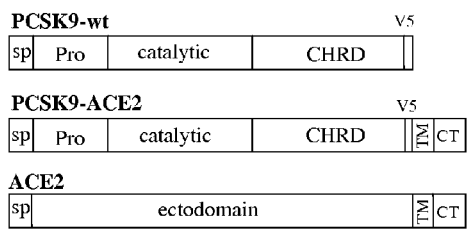
FIG. 1 shows stable PCSK9-wt and PCSK9-ACE2 expression in HuH7 cells. (A) schematic representation of the recombinant proteins used in examples herein. sp: signal peptide; Pro: prosegment; CHRD: cysteine and histidine-rich domain; TM: transmembrane domain; CT: cytoplasmic tail.
Figure 1:
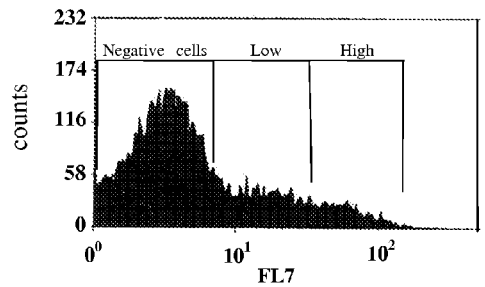
Figure 1:
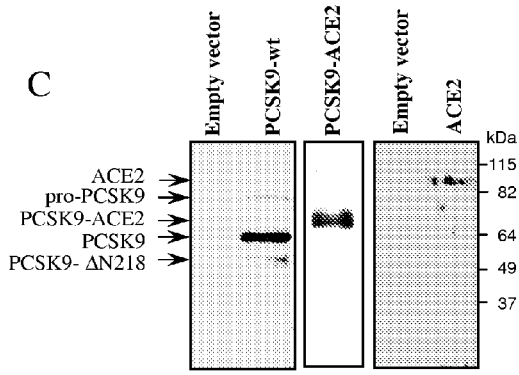
Figure 1:
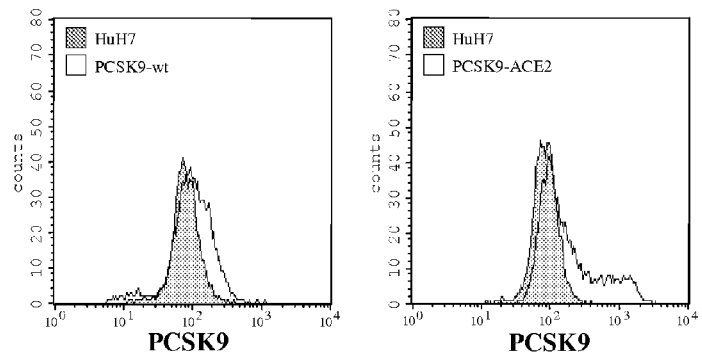
Figure 1:
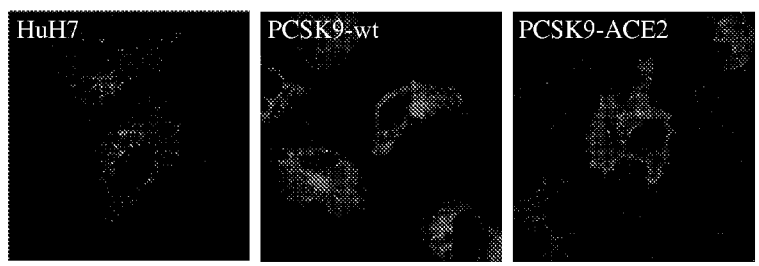

HuH7 cells stably expressing PCSK9-wt, PCSK9-ACE2, ACE2 or the empty vector phCMV3 were produced as described in Example 1 above in the section Plasmids and Stable Cell lines (FIG. 1A). All cells lines were sorted by FACS for the determination of their respective protein expression as described in Example 1 above in the section Flow cytometry, and the ~10% highest expressors were collected (FIG. 1B). The expression of the expected protein was confirmed by immunobloting of cell lysates (FIG. 1C). While PCSK9-wt is mostly secreted in the media, PCSK9-ACE2 remained attached to the cell surface through the transmembrane domain of ACE2 (FIG. 1D). Indirect immunofluorescence performed as described in Example 1 above of these stable cells using a PCSK9 polyclonal antibody (1/200) and a goat anti-rabbit-Alexa 488 (1/1000) using a confocal microscope revealed that just like PCSK9-wt, the chimeric protein PCSK9-ACE2 is detected in perinuclear locations (reminiscent of the endoplasmic reticulum), but is also abundantly concentrated at the cell surface (FIG. 1E) (70, 72). This association of PCSK9-ACE2 with the membrane greatly increases its ability to enhance the degradation of membrane-bound LDLR (70; 72).

The measurement of LDLR at the cell surface is then a good indicator of the PCSK9 activity. FACS analysis of the stable cell lines further demonstrated that while expression of ACE2 had no effect on cell surface LDLR, expression of PCSK9 and more so, PCSK9-ACE2 in HuH7 cells, resulted in a marked reduction in the amount of cell-surface LDLR (FIG. 2).

EXAMPLE 3

PCSK9 Expression in HuH7 Cells Inhibits Infection by HCVcc

The effect of PCSK9 on HCV propagation 3 days post-infection was then evaluated by recording the number of foci of infection. The number of foci of infection represents the number of infectious particles that successfully infect cells in a culture. Once within the cell, the virus will replicate and spread to the surrounding cells and form what appear as a cluster of infected cells also called a colony. Immunofluorescence performed as described in Example 1 above revealed that cells expressing PCSK9-ACE2 and, to a lesser extent PCSK9-wt, had a reduced number of foci expressing NS5A, as compared to HuH7 cells expressing ACE2 alone or the empty vector (phcmv3) (FIG. 3). HuH7 cells stably expressing PCSK9-ACE2 are more resistant to HCVcc since only very rare single cells are stained for NS5A and no colony could be detected.

To ensure that the TM-CT domain of ACE2 in the construct PCSK9-ACE2 was not accountable for the inhibition of infection, the full-length ACE2 protein was used as control. Results clearly indicated that ACE2 protein by itself has no effect on the permissiveness of the cells. Rather, it is believed that the TM-CT domain of ACE2 allows the concentration of PCSK9 at the cell surface (72). Therefore, PCSK9-wt and PCSK9-ACE2 were able to reduce both the size and the number of foci at 3 days post-infection. As expected, wild type PCSK9 was less efficient at inhibiting HCVcc infection than PCSK9-ACE2, likely due to its rapid secretion (3, 6, 29).

EXAMPLE 4

PCSK9 Inhibition Persists in Long-Term Infections

To determine if the continuous expression of high levels of PCSK9-wt and PCSK9-ACE2 could interfere with HCV infection, different HuH7 cell populations were infected with the HCVcc JFH-1 for 15 days. Infection of HuH7 cells by HCVcc JFH-1 has been well documented and the viral production peak is usually obtained several days post infection (69). FIG. 4A showed that at 15 days post infection there was still no detection (<1%) of the viral non-structural protein NS5A within HuH7 cells expressing PCSK9-ACE2, and a marked reduction (<8%) in HuH7 cells expressing PCSK9-wt. The remaining NS5A expression was quantitated following normalization of the emitted chemiluminescense of the NS5A protein with respect to β-actin levels (FIG. 4B).

The above estimation of the remaining infectivity was further confirmed by quantitative RT-PCR performed as described in Example 1 above in the section Quantitative RT-PCR (FIG. 4C). The level of the viral genome was reduced in cells expressing PCSK9-wt (>90% reduction). Notably, expression of the more active form, PCSK9-ACE2, almost completely blocked HCV infection (>99.9% reduction). This results shows that PCSK9-ACE2 not only blocks the infectivity in a short infection period, but also strongly inhibits the viral burden following a long infection period.

EXAMPLE 5

PCSK9 is Responsible for the Observed Inhibition

Confirmation that the effect observed on the viral replication was due to a bona fide PCSK9 protein activity and not to a cell defect that appeared during the selection of the cell population was then performed as follows. Naïve HuH7 cells were pre-incubated with purified soluble PCSK9 (FIG. 5B) added 4 h prior to infection at concentrations of 0, 0.12, 7.5 or 15 µg/ml (FIG. 5A). A concentration of 15 µg/ml of PCSK9 shown to be optimal for the reduction of cell-surface LDLR was used as the highest dose. Manual counting of the number of infection foci detected by immunofluorescence revealed that pure PCSK9 added to the media of HuH7 cells can inhibit HCV infection up to 2.5-fold in a dose-dependent manner (FIG. 5B).

EXAMPLE 6

PCSK9 Expression Removes Both LDLR and CD81 from the Cell Surface

The fate of the cell surface expression of CD81 and SR-BI two HCV receptors shown to be important for HCV infectivity in vitro (73, 74) was also analyzed. Thus, the cell surface CD81 and SR-BI levels were compared in HuH7 cell expressing PCSK9-wt, PCSK9-ACE2, ACE2 or an empty-vector. FACS analysis performed as described in Example 1 above revealed that PCSK9-wt and PCSK9-ACE2 not only reduced the LDLR protein level but also that of CD81 (FIG. 6). Interestingly, SR-BI expression was not affected in HuH7 expressing the empty vector, ACE2 or PCSK9-wt, but had a higher level of expression in HuH7 PCSK9-ACE2 cells (FIG. 6). It has previously been reported that a compensatory increase in SR-BI can occur in the context of reduced CD81 expression (75).

EXAMPLE 7

PCSK9-ACE2 Inhibits HCVpp Infection

To determine whether CD81 or LDLR or both were responsible for HCVcc inhibition in PCSK9 positive cells, HCV pseudoparticles (HCVpp) and VSV pseudoparticles (VSVpp) were used as control. HCVpp are produced in HEK293 cells and are devoid of lipoproteins on their surface, which impedes their interaction with the LDLR (76). Therefore, HCVpp infection is thought to be mainly mediated through the CD81 receptor (50). HCVpp were thus produced and their infectivity tested as described in Example 1 above in the section HCV pseudoparticles production and Pseudotyped Virus Infectivity Assays.

The results presented in FIG. 7 show that HCVpp can easily infect normal HuH7 cells or the ACE2 control cells, but not cells expressing the PCSK9-ACE2 protein (>80% inhibition). Therefore, with HCVpp, the reduction in infectivity seems to correlate with CD81 expression.

EXAMPLE 8

CD81 Protein could No Longer be Detected in Cells Expressing PCSK9

To further examine the effects of PCSK9 expression, the intracellular distribution of CD81 upon transient transfection of HuH7 cells with PCSK9-wt, PCSK9-ACE2 and PCSK9-Lamp1 was determined (72). Transient transfections were used instead of stable cell lines in order to compare side-by-side HuH7 cells with similar levels of the different PCSK9 forms. Under these conditions, the various forms of PCSK9 were readily visualized using a PCSK9 antibody, namely Ab1-hPC9 as described in Example 1 above at 48 h post transfection in all transfected cells (FIG. 8). Transfected cells represented ~30% of all HuH7 cells, a number compatible with the known low transfectability of these cells (72).

In agreement with Examples above, CD81 was completely absent in a large proportion of cells expressing either forms of PCSK9 (FIGS. 8F, I, L). The loss of CD81 is dependent of PCSK9 expression since all cells transfected with the control plasmid do express CD81 (FIG. 8B). This observation implies that the expression of PCSK9 resulted in the disappearance of the CD81 protein within the cells, but not in neighbouring ones. This suggests that it is the cellular PCSK9 that is most effective in enhancing the loss of CD81 expression.

EXAMPLE 9

PCSK9 Removes CD81 in an LDLR-Independent Manner

To further define the implication of the LDLR in the CD81 enhanced degradation by PCSK9, the level of LDLR in PCSK9-ACE2 expressing cells was reduced using a knockdown approach. For that purpose, two siRNAs (A and B) directed against the LDLR were tested as described in Example 1 above in the section LDLR siRNA Assay. The results showed that only siRNA-A significantly reduced LDLR expression (>78%) (FIG. 9A).

To investigate the molecular interaction between PCSK9, LDLR and CD81, naïve HuH7 cells and HuH7 cells stably expressing PCSK9-ACE2 were incubated with siRNA-A and the levels of CD81 was quantitated (FIG. 9B). The CD81 detected by the 5A6 monoclonal antibody appeared as two bands migrating with molecular masses below ~21 kDa, compared to the theoretically expected 24-26 kDa protein, as was previously observed in HuH7 cells (77, 78). As shown in FIG. 9B, knockdown of LDLR mRNA does not affect the level of immunoreactive CD81 in HuH7 cells, whereas in PCSK9-ACE2 cells, CD81 expression is significantly diminished (>79%).

EXAMPLE 10

Analysis of CD81 in the Liver of PCSK9 KO Mice

In order to assess whether the observed ex vivo effect of PCSK9 on CD81 in HuH7 cells would be the same in vivo, the levels of LDLR and CD81 was analyzed by indirect immunofluorescence in liver sections of single Pcsk9$^{-/-}$ and double [Pcsk9$^{-/-}$+Ldlr$^{-/-}$] knockout mice prepared as described previously (79).

Immunofluorescence of 10 µm thick liver cryosections from two different mice for each genotype, revealed that the labelling of CD81 appeared noticeably higher over the basolateral membrane of hepatocytes, facing sinusoids, in the Pcsk9$^{-/-}$ mice, as compared to that in wild type mice (FIG. 10, middle panels).

To further confirm that the effect of PCSK9 on CD81 is LDLR-independent, the CD81 expression in the liver of double knockout mice lacking both PCSK9 and LDLR was also analyzed (79). Here also, the level of CD81 was distinctly higher in the liver of double KO mice when compared to wt animals, suggesting that PCSK9 downregulates CD81 independently from the LDLR. These experiments were also repeated with a different antibody against CD81 (Hamster anti-CD81 (EAT1) ½0, Santa-Cruz), and generated similar results (not shown). As control, LDLR was visualized in the same mice and LDLR was observed to be highly expressed in the liver of Pcsk9$^{-/-}$ mice (FIG. 10B). These results clearly extend the ex vivo effect of PCSK9 in hepatocytes towards the realm of its regulation of the levels of hepatic CD81 in vivo.

EXAMPLE 11

Effect of PCSK9 Activity on HIV Replication

The effect of PCSK9 on HIV replication was evaluated using cells co-transfected with HIV constructions driving the expression of HIV genome combined with a construction allowing the expression of the different PCSK9 (e.g., PCSK9 and PCSK9-ACE2). HEK 293 cells were co-transfected and, at different times post infection, the level of viral particles released in the culture media (by any of the following assays, RT-PCR for HIV RNA genome, ELISA, etc.) was measured. The presence of PCSK9 reduced the level of viral particle as compared to the one in parallel control cells e.g., co-transfected with the empty vector.

EXAMPLE 12

Screening for Compounds Increasing the PCSK9 Activities

PCSK9 cell-based screening assay selective for cellular PCSK9 activities is used. In this functional cellular assay, the PCSK9 protein is modified to artificially decrease its activity against target receptors. The cell line harbors a high level of at least one cell surface receptor, such as LDLR and/or CD81. In a specific assay, the presence of a PCSK9 activator is detected by measuring a reduction of LDLR at the cell surface.

Any method specifically measuring the presence at the cell surface of LDLR, and/or other sensitive receptors, either alone or in combination, could be used. Methods include amongst others measuring the level of each type of receptors by using, antibodies labelled with a variety of light emitting systems, e.g., fluorochromes or chemiluminescent probes as well as western blot using the cell lysates.

Cells are incubated in the presence or absence of the candidate compounds and the effect on the level of LDLR or CD81 for example, is measured. A decrease in the level of LDLR, CD81 or of other PCSK9-susceptible receptors, in the presence of compound compared to the level measured in its absence is indicative that the compounds may increase or mimic the activity of PCSK9.

Alternatively, since PCSK9 could enter into cells when added to the culture supernatant and induce the degradation of LDLR, CD81 or of others susceptible receptors, and since HEK293 cells do not express endogenously PCSK9, cells are incubated with different peptides derived from PSCK9 or other candidate compounds in order to identify the smallest domain mediating the effect on cell surface receptor. A decrease in the level of LDLR or CD81, or other PCSK9-susceptible receptors, in the presence of the candidate peptide or other compound compared to the level measured in its absence is indicative that the candidate peptide or other compound may increase or mimic the activity of PCSK9.

Candidate modulators are screened on PCSK9 Cell-Based Assays. Compounds showing statistically significant activity are selected as hit compounds. Hit compounds are then further characterized for their effect on PCSK9 activity. In addition to the screening process itself, Quantitative Structure-Activity Relationship (QSAR) studies on hits are performed. Particularly, inhibitors with Kis in the nanomolar range are sought. In vitro and ex vivo validation and characterization of the lead compounds confirm their potency, specificity and effects.

EXAMPLE 13

Optimization of Leads

Once modulator "leads" are identified, they will be further characterized for affinity, mode of inhibition and specificity using in vitro assays and purified PC enzymes.

A modulator may be administered as monotherapy or separately, sequentially or simultaneously in combination with one or more anti-viral agents. Such anti-viral agents may be interferon and/or ribavirin. The combination of such compounds enhances the likelihood of substantially eliminating the virus from an individual.

Although the present invention has been described hereinabove by way of specific embodiments thereof, it can be modified, without departing from the spirit and nature of the subject invention as defined in the appended claims.

REFERENCES

1. Seidah, N. G. and Chretien, M. (1999) *Brain Res.* 848, 45-62.
2. Seidah, N. G. and Prat, A. (2002) *Essays Biochem.* 38, 79-94.
3. Seidah, N. G., Benjannet, S., Wickham, L., Marcinkiewicz, J., Jasmin, S. B., Stifani, S., Basak, A., Prat, A., and Chretien, M. (2003) *Proc. Natl. Acad. Sci. U.S.A* 100, 928-933.
4. Seidah, N. G., Mowla, S. J., Hamelin, J., Mamarbachi, A. M., Benjannet, S., Toure, B. B., Basak, A., Munzer, J. S., Marcinkiewicz, J., Zhong, M., Barale, J. C., Lazure, C., Murphy, R. A., Chretien, M., and Marcinkiewicz, M. (1999) *Proc. Natl. Acad. Sci. U.S.A* 96, 1321-1326.
5. Seidah, N. G., Khatib, A. M., and Prat, A. The proprotein convertases and their implication in sterol and/or lipid metabolism. Biological Chemistry (in press). 2006.
6. Benjannet, S., Rhainds, D., Essalmani, R., Mayne, J., Wickham, L., Jin, W., Asselin, M. C., Hamelin, J., Varret, M., Allard, D., Trillard, M., Abifadel, M., Tebon, A., Attie, A. D., Rader, D. J., Boileau, C., Brissette, L., Chretien, M., Prat, A., and Seidah, N. G. (2004) *J. Biol. Chem.* 279, 48865-48875.
7. Jin, W., Fuki, I. V., Seidah, N. G., Benjannet, S., Glick, J. M., and Rader, D. J. (2005) *J. Biol. Chem.* 280, 36551-36559.
8. Cheng, D., Espenshade, P. J., Slaughter, C. A., Jaen, J. C., Brown, M. S., and Goldstein, J. L. (1999) *J. Biol. Chem.* 274, 22805-22812.
9. Maxwell, K. N. and Breslow, J. L. (2004) *Proc. Natl. Acad. Sci. U.S.A* 101, 7100-7105.
10. Park, S. W., Moon, Y. A., and Horton, J. D. (2004) *J. Biol. Chem.* 279, 50630-50638.

11. Maxwell, K. N., Fisher, E. A., and Breslow, J. L. (2005) *Proc. Natl. Acad. Sci. U.S.A* 102, 2069-2074.
12. Zhong, M., Munzer, J. S., Basak, A., Benjannet, S., Mowla, S. J., Decroly, E., Chretien, M., and Seidah, N. G. (1999) *J. Biol. Chem.* 274, 33913-33920.
13. Nour, N., Basak, A., Chretien, M., and Seidah, N. G. (2003) *J. Biol. Chem.* 278, 2886-2895.
14. Pullikotil, P., Vincent, M., Nichol, S. T., and Seidah, N. G. (2004) *J. Biol. Chem.* 279, 17338-17347.
15. Benjannet, S., Savaria, D., Laslop, A., Munzer, J. S., Chretien, M., Marcinkiewicz, M., and Seidah, N. G. (1997) *J. Biol. Chem.* 272, 26210-26218.
16. Anderson, E. D., Thomas, L., Hayflick, J. S., and Thomas, G. (1993) *J. Biol. Chem.* 268, 24887-24891.
17. Seidah, N. G. (2006) *Biochem. J* 393, e1-e3.
18. Krug, R. M. (2006) *Science* 311, 1562-1563.
19. Lenz, O., ter Meulen, J., Klenk, H. D., Seidah, N. G., and Garten, W. (2001) *Proc. Natl. Acad. Sci. U.S.A* 98, 12701-12705.
20. Beyer, W. R., Popplau, D., Garten, W., Von Laer, D., and Lenz, O. (2003) *J. Virol.* 77, 2866-2872.
21. Vincent, M. J., Sanchez, A. J., Erickson, B. R., Basak, A., Chretien, M., Seidah, N. G., and Nichol, S. T. (2003) *J. Virol.* 77, 8640-8649.
22. Henrich, S., Cameron, A., Bourenkov, G. P., Kiefersauer, R., Huber, R., Lindberg, I., Bode, W., and Than, M. E. (2003) *Nat. Struct. Biol.* 10, 520-526.
23. Simmons, G., Gosalia, D. N., Rennekamp, A. J., Reeves, J. D., Diamond, S. L., and Bates, P. (2005) *Proc. Natl. Acad. Sci. U.S.A* 102, 11876-11881.
24. Pager, C. T. and Dutch, R. E. (2005) *J. Virol.* 79, 12714-12720.
25. Chandran, K., Sullivan, N. J., Felbor, U., Whelan, S. P., and Cunningham, J. M. (2005) *Science* 308, 1643-1645.
26. Maxwell, K. N., Soccio, R. E., Duncan, E. M., Sehayek, E., and Breslow, J. L. (2003) *J. Lipid Res.* 44, 2109-2119.
27. Dubuc, G., Chamberland, A., Wassef, H., Davignon, J., Seidah, N. G., Bernier, L., and Prat, A. (2004) *Arterioscler. Thromb. Vasc. Biol.* 24, 1454-1459.
28. Horton, J. D., Shah, N. A., Warrington, J. A., Anderson, N. N., Park, S. W., Brown, M. S., and Goldstein, J. L. (2003) *Proc. Natl. Acad. Sci. U.S.A* 100, 12027-12032.
29. Benjannet, S., Rhainds, D., Hamelin, J., Nassoury, N., and Seidah, N. G. (2006) *J. Biol. Chem.* 281, 30561-30572.
30. Lagace, T. A., Curtis, D. E., Garuti, R., McNutt, M. C., Park, S. W., Prather, H. B., Anderson, N. N., Ho, Y. K., Hammer, R. E., and Horton, J. D. (2006) *J. Clin. Invest* 116, 2995-3005.
31. Attie, A. D. (2004) *Arterioscler. Thromb. Vasc. Biol.* 24, 1337-1339.
32. Abifadel, M., Varret, M., Rabes, J. P., Allard, D., Ouguerram, K., Devillers, M., Cruaud, C., Benjannet, S., Wickham, L., Erlich, D., Derre, A., Villeger, L., Farnier, M., Beucler, I., Bruckert, E., Chambaz, J., Chanu, B., Lecerf, J. M., Luc, G., Moulin, P., Weissenbach, J., Prat, A., Krempf, M., Junien, C., Seidah, N. G., and Boileau, C. (2003) *Nat. Genet.* 34, 154-156.
33. Leren, T. P. (2004) *Clin. Genet.* 65, 419-422.
34. Timms, K. M., Wagner, S., Samuels, M. E., Forbey, K., Goldfine, H., Jammulapati, S., Skolnick, M. H., Hopkins, P. N., Hunt, S. C., and Shattuck, D. M. (2004) *Hum. Genet.* 114, 349-353.
35. Allard, D., Amsellem, S., Abifadel, M., Trillard, M., Devillers, M., Luc, G., Krempf, M., Reznik, Y., Girardet, J. P., Fredenrich, A., Junien, C., Varret, M., Boileau, C., Benlian, P., and Rabes, J. P. (2005) *Hum. Mutat.* 26, 497-506.
36. Naoumova, R. P., Tosi, I., Patel, D., Neuwirth, C., Horswell, S. D., Marais, A. D., van Heyningen, C., and Soutar, A. K. (2005) *Arterioscler. Thromb. Vasc. Biol.* 25, 2654-2660.
37. Cohen, J., Pertsemlidis, A., Kotowski, I. K., Graham, R., Garcia, C. K., and Hobbs, H. H. (2005) *Nat. Genet.* 37, 161-165.
38. Kotowski, I. K., Pertsemlidis, A., Luke, A., Cooper, R. S., Vega, G. L., Cohen, J. C., and Hobbs, H. H. (2006) *Am. J. Hum. Genet.* 78, 410-422.
39. Berge, K. E., Ose, L., and Leren, T. P. (2006) *Arterioscler. Thromb. Vasc. Biol.* 26, 1094-10100.
40. Attie, A. D. and Seidah, N. G. (2005) *Cell Metab* 1, 290-292.
41. Rashid, S., Curtis, D. E., Garuti, R., Anderson, N. N., Bashmakov, Y., Ho, Y. K., Hammer, R. E., Moon, Y. A., and Horton, J. D. (2005) *Proc. Natl. Acad. Sci. U.S.A* 102, 5374-5379.
42. Lalanne, F., Lambert, G., Amar, M. J., Chetiveaux, M., Zair, Y., Jarnoux, A. L., Ouguerram, K., Friburg, J., Seidah, N. G., Brewer, H. B., Jr., Krempf, M., and Costet, P. (2005) *J. Lipid Res.* 46, 1312-1319.
43. Laird, F. M., Cai, H., Savonenko, A. V., Farah, M. H., He, K., Melnikova, T., Wen, H., Chiang, H. C., Xu, G., Koliatsos, V. E., Borchelt, D. R., Price, D. L., Lee, H. K., and Wong, P. C. (2005) *J. Neurosci.* 25, 11693-11709.
44. Fatemi, S. H. (2005) *Int. Rev. Neurobiol.* 71, 179-187.
45. Thomson, B. J., and Finch, R, G. (2005). *Clin. Microbiol. Infect.* 11, 86-94.
46. Poynard, T., Yuen, M. F., Ratziu, V., and Lai, C. L. (2003). *Lancet* 362, 2095-2100.
47. Simmonds, P., Bukh, J., Combet, Deleage, G., Enomoto, N., Feinstone, S., Halfon, P., Inchauspe, G., Kuiken, C., Maertens, G., Mizokami, M., Murphy, D. G., Okamoto, H., Pawlotsky, J. M., Penin, F., Sablon, E., Shin, I., Stuyver, L. J., Thiel, H. J., Viazov, S., Weiner, A. J., and Widell, A. (2005). *Hepatology* 42, 962-973.
48. Bartenschlager, R., Frese, M., and Pietschmann, T. (2004). *Adv. Virus. Res.* 63, 71-180.
49. Diedrich, G. (2006) *FEBS J.* 273, 3871-3885.
50. Bartosch, B., and Cosset, F. L. (2006) *Virology* 348, 1-12.
51. Pileri, P., Uematsu, Y., Campagnoli, S., Galli, G., Falugi, F., Petracca, R., Weiner, A. J., Houghton, M., Rosa, D., Grandi, G., and Abrignani, S. (1998). *Science.* 282, 938-941.
52. Scarselli, E., Ansuini, H., Cerino, R., Roccasecca, R. M., Acali, S., Filocamo, G., Traboni, C., Nicosia, A., Cortese, R., and Vitelli, A. (2002). *EMBO J.* 21, 5017-5025.
53. Wünschmann, S., Medh, J. D., Klinzmann, D., Schmidt, W. N., and Stapleton, J. T. (2000). *J. Virol.* 74, 10055-10062.
54. Agnello, V., Abel, G., Elfahal, M., Knight, G. B., and Zhang, Q. X. (1999). *Proc Natl Acad Sci USA.* 96, 12766-12771.
55. Evans, M. J., von Hahn, T., Tscherne, D. M., Syder, A. J., Panis, M., Wölk, B., Hatziioannou, T., McKeating, J. A., Bieniasz, P. D., and Rice, C. M. (2007). *Nature.* 446, 801-805.
56. Barth, H., Schnober, E. K., Zhang, F., Linhardt, R. J., Depla, E., Boson, B., Cosset, F. L., Patel, A. H., Blum, H. E., and Baumert, T. F. (2006) *J. Virol.* 80, 10579-10590.
57. Nielsen, S. U., Bassendine, M. F., Burt, A. D., Martin, C., Pumeechockchai, W., and Toms, G. L. (2006). *J. Virol.* 80, 2418-2428.
58. André, P., Komurian-Pradel, F., Deforges, S., Perret, M., Berland, J. L., Sodoyer, M., Pol, S., Bréchot, C., Paranhos-Baccalà, G., and Lotteau, V. (2002) *J. Virol.* 76, 6919-6928.

59. Siagris, D., Christofidou, M., Theocharis, G. J., Pagoni, N., Papadimitriou, C., Lekkou, A., Thomopoulos, K., Starakis, I., Tsamandas, A. C., and Labropoulou-Karatza, C. (2006) *J Viral Hepat.* 13, 56-61.
60. Ye, J., Wang, C., Sumpter, R. Jr., Brown, M. S., Goldstein, J. L., and Gale, M. Jr. (2003) *Proc Natl. Acad. Sci. USA* 100, 15865-15870.
61. Andréo, U., Maillard, P., Kalinina, O., Walic, M., Meurs, E., Martinot, M., Marcellin, P., and Budkowska, A. (2007) *Cell Microbiol.* 9, 2445-2456.
62. Gower, T. L., and Graham, B. S. *AntiMicrob. Agents and Chemother.* (2001) 45, 1231-1237.
63. Glenn, J. S., Marsters, J. C. Jr., Greenberg, H. B., (1998) *J. Virol.* 72, 9303-9306;
64. Black, D. M., Bakker-Arkema, R. G., and; James W. Nawrocki, J. W. (1998) *Arch. Inter. Med.* 158, 577-584.
65. Jolly, C. and Sattentau, Q. J. (2007) *J. Virol.* 81, 7873-7884.
66. Lazo, P. A. (2007) *Cancer Sci.*
67. Berditchevski, F. and Odintsova, E. (2007) *Traffic.* 8, 89-96.
68. Heller, T., Saito, S., Auerbach, J., Williams, T., Moreen, T. R., Jazwinski, A., Cruz, B., Jeurkar, N., Sapp, R., Luo, G., and Liang, T. J. (2005) *Proc. Natl. Acad. Sci. U.S.A* 102, 2579-2583.
69. Wakita, T., Pietschmann, T., Kato, T., Date, T., Miyamoto, M., Zhao, Z., Murthy, K., Habermann, A., Krausslich, H. G., Mizokami, M., Bartenschlager, R., and Liang, T. J. (2005) *Nat. Med.* 11, 791-796.
70. Nassoury, N., Blasiole, D. A., Tebon, O. A., Benjannet, S., Hamelin, J., Poupon, V., McPherson, P. S., Attie, A. D., Prat, A., and Seidah, N. G. (2007) *Traffic.* 8, 718-732.
71. Akazawa, D., Date, T., Morikawa, K., Murayama, A., Miyamoto, M., Kaga, M., Barth, H., Baumert, T. F., Dubuisson, J., and Wakita, T. (2007) *J Virol* 81, 5036-5045.
72. Poirier, S., Mayer, G., Benjannet, S., Bergeron, E., Marcinkiewicz, J., Nassoury, N., Mayer, H., Nimpf, J., Prat, A., and Seidah, N. G. (2008) *J Biol Chem* 283, 2363-2372.
73. Zeisel, M. B., Koutsoudakis, G., Schnober, E. K., Haberstroh, A., Blum, H. E., Cosset, F. L., Wakita, T., Jaeck, D., Doffoel, M., Royer, C., Soulier, E., Schvoerer, E., Schuster, C., Stoll-Keller, F., Bartenschlager, R., Pietschmann, T., Barth, H., and Baumert, T. F. (2007) *Hepatology* 46, 1722-1731.
74. Petit, J. M., Minello, A., Duvillard, L., Jooste, V., Monier, S., Texier, V., Bour, J. B., Poussier, A., Gambert, P., Verges, B., and Hillon, P. (2007) *Am J Physiol Endocrinol Metab* 293, E416-420.
75. Kapadia, S. B., Barth, H., Baumert, T., McKeating, J. A., and Chisari, F. V. (2007) *J Virol* 81, 374-383.
76. Lavillette, D., Bartosch, B., Nourrisson, D., Verney, G., Cosset, F. L., Penin, F., and Pecheur, E. I. (2006) *J Biol Chem* 281, 3909-3917.
77. Rocha-Perugini, V., Montpellier, C., Delgrange, D., Wychowski, C., Helle, F., Pillez, A., Drobecq, H., Le Naour, F., Charrin, S., Levy, S., Rubinstein, E., Dubuisson, J., and Cocquerel, L. (2008) *PLoS ONE* 3, e1866.
78. Jamshad, M., Rajesh, S., Stamataki, Z., McKeating, J. A., Dafform, T., Overduin, M., and Bill, R. M. (2008) *Protein Expr Purif* 57, 206-216.
79. Zaid, A., Roubtsova, A., Essalmani, R., Marcinkiewicz, J., Chamberland, A., Hamelin, J., Tremblay, M., Jacques, H., Jin, W., Davignon, J., Seidah, N. G., and Prat, A. (2008) *Hepatology* 48, 646-654.

---

The invention claimed is:

1. A method for inhibiting sustained hepatitis C virus (HCV) replication in a host infected by HCV, said method comprising decreasing the expression of CD81 at the surface of cells from said host by administering a composition comprising a proprotein convertase subtilisin/kexin type 9 preproprotein (PCSK9) in the host infected by HCV, whereby the increased PCSK9 activity inhibits sustained HCV replication in the host, and wherein said PCSK9 comprises a sequence as set forth between residues 153 to 692 of SEQ ID NO:2.

2. The method of claim 1, wherein the host comprises hepatocytes or immune cells.

3. The method of claim 1, wherein the host is cells, a tissue, or an organ.

4. The method of claim 3, wherein said cells are hepatocytes.

5. The method of claim 3, wherein said organ is liver.

* * * * *

SEQUENCE LISTING

```
<160> NUMBER OF SEQ ID NOS: 9

<210> SEQ ID NO 1
<211> LENGTH: 2124
<212> TYPE: DNA
<213> ORGANISM: artificial sequence
<220> FEATURE:
<223> OTHER INFORMATION: PCSK9 with V5 tag

<400> SEQUENCE: 1
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgttc cgaggaggac ggcctggccg aagcacccga gcacggaacc     180
acagccacct tccaccgctg cgccaaggat ccgtggaggt tgcctggcac ctacgtggtg     240
gtgctgaagg aggagaccca cctctcgcag tcagagcgca ctgcccgccg cctgcaggcc     300
caggctgccc gcgggggata cctcaccaag atcctgcatg tcttccatgg ccttcttcct     360
ggcttcctgg tgaagatgag tggcgacctg ctggagctgg ccttgaagtt gccccatgtc     420
gactacatcg aggaggactc ctctgtcttt gcccagagca tcccgtggaa cctggagcgg     480 attcccctc cacggtaccg ggcggatgaa taccagcccc ccgacggagg cagcctggtg     540
gaggtgtatc tcctagacac cagcatacag agtgaccacc gggaaatcga gggcagggtc     600
atggtcaccg acttcgagaa tgtgcccgag gaggacggga cccgcttcca cagacaggcc     660
agcaagtgtg acagtcatgg cacccacctg gcaggggtgg tcagcggccg ggatgccggc     720
```

```
gtggccaagg gtgccagcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgagac    960
gatgcctgcc tctactcccc agcctcagct cccgaggtca tcacagttgg ggccaccaat   1020
gcccaggacc agccggtgac cctggggact ttggggacca ctttggccg ctgtgtggac    1080 ctctttgccc caggggagga catcattggt gcctccagcg actgcagcac ctgctttgtg   1140
tcacagagtg ggacatcaca ggctgctgcc cacgtggctg gcattgcagc catgatgctg   1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgcccccag cacccatggg gcaggttggc agctgttttg caggactgtg    1380
tggtcagcac actcggggcc tacacggatg ccacagcca tcgcccgctg cgccccagat    1440
gaggagctgc tgagctgctc cagtttctcc aggagtggga gcggcgggg cgagcgcatg    1500 gaggcccaag ggggcaagct ggtctgccgg gcccacaacg cttttggggg tgagggtgtc   1560
tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacaggagg ccagcatcca cgcttcctgc    1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctgggggc ctacgccgta gacaacacgt gtgtagtcag gagccgggac   1980
gtcagcacta caggcagcac cagcgaagag gccgtgacag ccgttgccat ctgctgccgg   2040
agccggcacc tggcgcaggc ctcccaggag ctacagaccg gtaagcctat ccctaaccct   2100
ctcctcggtc tcgattctac gtga                                          2124
```

<210> SEQ ID NO 2
<211> LENGTH: 707
<212> TYPE: PRT
<213> ORGANISM: artificial sequence
<220> FEATURE:
<223> OTHER INFORMATION: PCSK9 with V5 tag

<400> SEQUENCE: 2

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
```

```
              115                 120                 125
Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
530                 535                 540
```

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
            565                 570                 575

Pro Val Leu Arg Pro Arg Gly Gln Pro Asn Gln Cys Val Gly His Arg
        580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
            645                 650                 655

Arg Ser Arg Asp Val Ser Thr Thr Gly Ser Thr Ser Glu Glu Ala Val
        660                 665                 670

Thr Ala Val Ala Ile Cys Cys Arg Ser Arg His Leu Ala Gln Ala Ser
            675                 680                 685

Gln Glu Leu Gln Thr Gly Lys Pro Ile Pro Asn Pro Leu Leu Gly Leu
690                 695                 700

Asp Ser Thr
705

<210> SEQ ID NO 3
<211> LENGTH: 2325
<212> TYPE: DNA
<213> ORGANISM: artificial sequence
<220> FEATURE:
<223> OTHER INFORMATION: PCSK9 fused to ACE2 TM-CT

<400> SEQUENCE: 3

```
atgggcaccg tcagctccag gcggtcctgg tggccgctgc cactgctgct gctgctgctg      60
ctgctcctgg gtcccgcggg cgcccgtgcg caggaggacg aggacggcga ctacgaggag     120
ctggtgctag ccttgcgttc cgaggaggac ggcctggccg aagcacccga gcacggaacc     180
acagccacct ccaccgctg cgccaaggat ccgtggaggt tgcctggcac ctacgtggtg     240
gtgctgaagg aggagaccca cctctcgcag tcagagcgca ctgcccgccg cctgcaggcc     300
caggctgccc gccggggata cctcaccaag atcctgcatg tcttccatgg ccttcttcct     360
ggcttcctgg tgaagatgag tggcgacctg ctggagctgg ccttgaagtt gccccatgtc     420
gactacatcg aggaggactc ctctgtcttt gcccagagca tcccgtggaa cctggagcgg     480 attcccctc acggtaccg gcggatgaa taccagcccc cgacggagg cagcctggtg     540 gaggtgtatc tcctagacac cagcatacag agtgaccacc gggaaatcga gggcagggtc     600
atggtcaccg acttcgagaa tgtgcccgag gaggacggga cccgcttcca cagacaggcc     660
agcaagtgtg acagtcatgg cacccacctg caggggtgg tcagcggccg ggatgccggc     720
gtggccaagg gtgccagcat gcgcagcctg cgcgtgctca actgccaagg gaagggcacg     780
gttagcggca ccctcatagg cctggagttt attcggaaaa gccagctggt ccagcctgtg     840
gggccactgg tggtgctgct gcccctggcg ggtgggtaca gccgcgtcct caacgccgcc     900
tgccagcgcc tggcgagggc tggggtcgtg ctggtcaccg ctgccggcaa cttccgagac     960
gatgcctgcc tctactcccc agcctcagct cccgaggtca tcacagttgg ggccaccaat    1020
gcccaggacc agccggtgac cctggggact ttggggacca ctttggcgc tgtgtggac    1080 ctctttgccc caggggagga catcattggt gcctccagcg actgcagcac tgctttgtg    1140
```

-continued

```
tcacagagtg ggacatcaca ggctgctgcc cacgtggctg gcattgcagc catgatgctg      1200
tctgccgagc cggagctcac cctggccgag ttgaggcaga gactgatcca cttctctgcc      1260
aaagatgtca tcaatgaggc ctggttccct gaggaccagc gggtactgac ccccaacctg      1320
gtggccgccc tgccccccag cacccatggg gcaggttggc agctgttttg caggactgtg      1380
tggtcagcac actcggggcc tacacggatg ccacagccca tcgcccgctg cgccccagat      1440
gaggagctgc tgagctgctc cagtttctcc aggagtggga gcggcggggc cgagcgcatg      1500
gaggcccaag ggggcaagct ggtctgccgg gcccacaacg cttttggggg tgagggtgtc      1560
tacgccattg ccaggtgctg cctgctaccc caggccaact gcagcgtcca cacagctcca      1620
ccagctgagg ccagcatggg gacccgtgtc cactgccacc aacagggcca cgtcctcaca      1680
ggctgcagct cccactggga ggtggaggac cttggcaccc acaagccgcc tgtgctgagg      1740
ccacgaggtc agcccaacca gtgcgtgggc cacaggggagg ccagcatcca cgcttcctgc      1800
tgccatgccc caggtctgga atgcaaagtc aaggagcatg gaatcccggc ccctcaggag      1860
caggtgaccg tggcctgcga ggagggctgg accctgactg gctgcagtgc cctccctggg      1920
acctcccacg tcctggggc ctacgccgta gacaacacgt gtgtagtcag agccgggac      1980 gtcagcacta caggcagcac cagcgaagag gccgtgacag ccgttgccat ctgctgccgg      2040
agccggcacc tggcgcaggc ctcccaggag ctccagaccg gtaagcctat ccctaaccct      2100
ctcctcggtc tcgattctac gggaggaata tggctgattg ttttttggagt tgtgatggga      2160 gtgatagtgg ttggcattgt catcctgatc ttcactggga tcagagatcg gaagaagaaa      2220
aataaagcaa gaagtggaga aaatccttat gcctccatcg atattagcaa aggagaaaat      2280
aatccaggat ccaaaaacac tgatgatgtt cagacctcct tttag                      2325
```

<210> SEQ ID NO 4
<211> LENGTH: 774
<212> TYPE: PRT
<213> ORGANISM: artificial sequence
<220> FEATURE:
<223> OTHER INFORMATION: PCSK9 fused to ACE2 TM-CT

<400> SEQUENCE: 4

```
Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160
```

```
Ile Thr Pro Pro Arg Tyr Arg Ala Asp Glu Tyr Gln Pro Pro Asp Gly
            165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
        210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
        290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
            325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
        370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
            405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
        450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
            485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
        530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
            565                 570                 575

Pro Val Leu Arg Pro Arg Gly Gln Pro Asn Gln Cys Val Gly His Arg
```

|  | 580 |  | 585 |  |  | 590 |  |  |  |
|---|---|---|---|---|---|---|---|---|---|
| Glu | Ala | Ser | Ile | His | Ala | Ser | Cys | Cys | His | Ala | Pro | Gly | Leu | Glu | Cys |
|  |  |  | 595 |  |  |  | 600 |  |  |  | 605 |  |  |  |  |

| Lys | Val | Lys | Glu | His | Gly | Ile | Pro | Ala | Pro | Gln | Glu | Gln | Val | Thr | Val |
|---|---|---|---|---|---|---|---|---|---|---|---|---|---|---|---|
|  | 610 |  |  |  |  | 615 |  |  |  |  | 620 |  |  |  |  |

| Ala | Cys | Glu | Glu | Gly | Trp | Thr | Leu | Thr | Gly | Cys | Ser | Ala | Leu | Pro | Gly |
|---|---|---|---|---|---|---|---|---|---|---|---|---|---|---|---|
| 625 |  |  |  |  | 630 |  |  |  |  | 635 |  |  |  |  | 640 |

Thr Ser His Val Leu Gly Ala Tyr Ala Val Asp Asn Thr Cys Val Val
                       645                    650                    655

Arg Ser Arg Asp Val Ser Thr Thr Gly Ser Thr Ser Glu Glu Ala Val
           660                    665                    670

Thr Ala Val Ala Ile Cys Cys Arg Ser Arg His Leu Ala Gln Ala Ser
             675                  680                  685

Gln Glu Leu Gln Thr Gly Lys Pro Ile Pro Asn Pro Leu Leu Gly Leu
     690                  695                  700

Asp Ser Thr Gly Gly Ile Trp Leu Ile Val Phe Gly Val Val Met Gly
705                  710                  715                720

Val Ile Val Val Gly Ile Val Ile Leu Ile Phe Thr Gly Ile Arg Asp
             725                  730                 735

Arg Lys Lys Lys Asn Lys Ala Arg Ser Gly Glu Asn Pro Tyr Ala Ser
         740                  745                  750

Ile Asp Ile Ser Lys Gly Glu Asn Asn Pro Gly Phe Gln Asn Thr Asp
             755                  760                765

Asp Val Gln Thr Ser Phe
     770

<210> SEQ ID NO 5
<211> LENGTH: 2235
<212> TYPE: DNA
<213> ORGANISM: artificial sequence
<220> FEATURE:
<223> OTHER INFORMATION: PCSK9 fused to LAMP1 TM-CT

<400> SEQUENCE: 5

| atgggcaccg | tcagctccag | gcggtcctgg | tggccgctgc | cactgctgct | gctgctgctg | 60 |
|---|---|---|---|---|---|---|
| ctgctcctgg | gtcccgcggg | cgcccgtgcg | caggaggacg | aggacggcga | ctacgaggag | 120 |
| ctggtgctag | ccttgcgttc | cgaggaggac | ggcctggccg | aagcacccga | gcacggaacc | 180 |
| acagccacct | tccaccgctg | cgccaaggat | ccgtggaggt | tgcctggcac | ctacgtggtg | 240 |
| gtgctgaagg | aggagaccca | cctctcgcag | tcagagcgca | ctgcccgccg | cctgcaggcc | 300 |
| caggctgccc | gccggggata | cctcaccaag | atcctgcatg | tcttccatgg | ccttcttcct | 360 |
| ggcttcctgg | tgaagatgag | tggcgacctg | ctggagctgg | ccttgaagtt | gccccatgtc | 420 |
| gactacatcg | aggaggactc | ctctgtcttt | gcccagagca | tcccgtggaa | cctggagcgg | 480 |
| attccccctc | acggtaccg | gcggatgaa | taccagcccc | cgacggagg | cagcctggtg | 540 |
| gaggtgtatc | tcctagacac | cagcatacag | agtgaccacc | gggaaatcga | gggcagggtc | 600 |
| atggtcaccg | acttcgagaa | tgtgcccgag | gaggacggga | cccgcttcca | cagacaggcc | 660 |
| agcaagtgtg | acagtcatgg | cacccacctg | gcaggggtgg | tcagcggccg | ggatgccggc | 720 |
| gtggccaagg | tgccggcat | gcgcagcctg | cgcgtgctca | actgccaagg | gaagggcacg | 780 |
| gttagcggca | ccctcatagg | cctggagttt | attcggaaaa | gccagctggt | ccagcctgtg | 840 |
| gggccactgg | tggtgctgct | gcccctggcg | ggtgggtaca | gccgcgtcct | caacgccgcc | 900 |
| tgccagcgcc | tggcgagggc | tggggtcgtg | ctggtcaccg | ctgccggcaa | cttccgagac | 960 |

```
gatgcctgcc tctactcccc agcctcagct cccgaggtca tcacagttgg ggccaccaat    1020
gcccaggacc agccggtgac cctggggact ttggggacca actttggccg ctgtgtggac    1080
ctctttgccc caggggagga catcattggt gcctccagcg actgcagcac ctgctttgtg    1140
tcacagagtg ggacatcaca ggctgctgcc cacgtggctg gcattgcagc catgatgctg    1200
tctgccgagc cggagctcac cctggccgag ttgaggcaga gactgatcca cttctctgcc    1260
aaagatgtca tcaatgaggc ctggttccct gaggaccagc gggtactgac ccccaacctg    1320
gtggccgccc tgccccccag cacccatggg gcaggttggc agctgttttg caggactgtg    1380
tggtcagcac actcggggcc tacacggatg ccacagccca tcgcccgctg cgccccagat    1440
gaggagctgc tgagctgctc cagtttctcc aggagtggga agcggcgggg cgagcgcatg    1500 gagcccaag gggcaagct ggtctgccgg gcccacaacg cttttggggg tgagggtgtc    1560
tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc acagggagg ccagcatcca cgcttcctgc    1800
tgccatgccc caggtctgga atgcaaagtc aaggagcatg aatcccggc ccctcaggag    1860 caggtgaccg tggcctgcga gggggctgg accctgactg gctgcagtgc cctccctggg    1920
acctcccacg tcctgggggc ctacgccgta gacaacacgt gtgtagtcag gagccgggac    1980
gtcagcacta caggcagcac cagcgaagag gccgtgacag ccgttgccat ctgctgccgg    2040
agccggcacc tggcgcaggc ctcccaggag ctccagaccg gtaagcctat ccctaaccct    2100
ctcctcggtc tcgattctac gggaggactg atccccatcg ctgtgggtgg tgccctggcg    2160
gggctggtcc tcatcgtcct catcgcctac ctcgtcggca ggaagaggag tcacgcaggc    2220
taccagacta tctag                                                     2235
```

<210> SEQ ID NO 6
<211> LENGTH: 744
<212> TYPE: PRT
<213> ORGANISM: artificial sequence
<220> FEATURE:
<223> OTHER INFORMATION: PCSK9 fused to LAMP1 TM-CT

<400> SEQUENCE: 6

```
Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140
```

```
Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Gly Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
```

```
                    565                 570                 575
Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln Thr Gly Lys Pro Ile Pro Asn Pro Leu Leu Gly Leu
    690                 695                 700

Asp Ser Thr Gly Gly Leu Ile Pro Ile Ala Val Gly Gly Ala Leu Ala
705                 710                 715                 720

Gly Leu Val Leu Ile Val Leu Ile Ala Tyr Leu Val Gly Arg Lys Arg
                725                 730                 735

Ser His Ala Gly Tyr Gln Thr Ile
            740

<210> SEQ ID NO 7
<211> LENGTH: 21
<212> TYPE: DNA
<213> ORGANISM: artificial sequence
<220> FEATURE:
<223> OTHER INFORMATION: PCR primer

<400> SEQUENCE: 7
gagtgggttt atccaagaaa g                                          21

<210> SEQ ID NO 8
<211> LENGTH: 18
<212> TYPE: DNA
<213> ORGANISM: artificial sequence
<220> FEATURE:
<223> OTHER INFORMATION: PCR primer

<400> SEQUENCE: 8
tctgcggaac cggtgagt                                              18

<210> SEQ ID NO 9
<211> LENGTH: 20
<212> TYPE: DNA
<213> ORGANISM: artificial sequence
<220> FEATURE:
<223> OTHER INFORMATION: PCR primer

<400> SEQUENCE: 9
cggaattgcc gggaagactg                                            20
```